(12) United States Patent
Guo et al.

(10) Patent No.: US 8,501,749 B2
(45) Date of Patent: Aug. 6, 2013

(54) AZAQUINAZOLINEDIONES CHYMASE INHIBITORS

(75) Inventors: Xin Guo, Danbury, CT (US); Chuk Chui Man, Ridgefield, CT (US); Hidenori Takahashi, LaGrangeville, NY (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 69 days.

(21) Appl. No.: 13/146,765

(22) PCT Filed: Jan. 26, 2010

(86) PCT No.: PCT/US2010/022052
§ 371 (c)(1),
(2), (4) Date: Nov. 29, 2011

(87) PCT Pub. No.: WO2010/088195
PCT Pub. Date: Aug. 5, 2010

(65) Prior Publication Data
US 2012/0108597 A1    May 3, 2012

Related U.S. Application Data

(60) Provisional application No. 61/148,693, filed on Jan. 30, 2009.

(51) Int. Cl.
*C07D 471/04* (2006.01)
*C07D 475/02* (2006.01)
*A61K 31/519* (2006.01)

(52) U.S. Cl.
USPC ............ 514/258.1; 514/262.1; 514/263.1; 514/264.1; 544/245; 544/256; 544/257; 544/279; 544/311

(58) Field of Classification Search
USPC ....... 544/245, 256, 257, 279, 311; 514/258.1, 514/262.1, 263.3, 264.1
See application file for complete search history.

(56) References Cited

FOREIGN PATENT DOCUMENTS
WO    2008/147697 A1    12/2008
WO    2009/023655 A1    2/2009

OTHER PUBLICATIONS

International Search Report for PCT/US2010/022052 mailed on Mar. 17, 2010.

*Primary Examiner* — Bruck Kifle
(74) *Attorney, Agent, or Firm* — Michael P. Morris; Usha R. Patel

(57) ABSTRACT

Disclosed are small molecule inhibitors of the formula (I), which are useful in treating various diseases and conditions involving chymase.

(I)

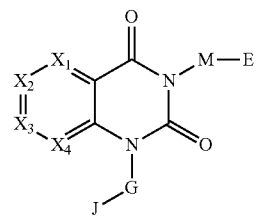

8 Claims, No Drawings

AZAQUINAZOLINEDIONES CHYMASE INHIBITORS

APPLICATION DATA

This application claims benefit to U.S. provisional application Ser. No. 61/148,693 filed Jan. 30, 2009.

FIELD OF THE INVENTION

The invention relates to small molecule inhibitors which are useful in treating various diseases and conditions involving Chymase.

BACKGROUND OF THE INVENTION

In cardiac tissue of cardiomyopathic patients, transforming growth factor-β (TGF-β), which has been demonstrated to stimulate cardiac fibrosis in animal models (Kuwahara, et al. Circulation, 2002, 106, 130), is increased (Li et al., Circulation, 1997, 96, 874). In the myocardial fibrotic area, it is known that mast cells are increased in number and may contribute to the development of fibroblast proliferation in cardiac tissues of patients with cardiomyopathy (Patella et al., Circulation, 1998, 97, 971). Chymase is a chymotrypsin-like serine protease contained in the secretory granules of mast cells. Although the precise physiological roles of Chymase have not been completely revealed, Chymase is known to transform angiotensin I to angiotensin II and may contribute to activation of TGF-β, matrix proteases, and cytokines (Taipale et al., J. Biol. Chem., 1995, 270, 4689; Takai et al., Life Sci., 1996, 58, 591; Takai et al., Circulation, 1999, 100, 654).

A potent and selective Chymase inhibitor may have potential use as a treatment of chronic heart failure, atherosclerosis, restenosis, and myocardial infarction by inhibiting local production of angiotensin II in the heart and release of TGF-β, two independent mediators of cardiac remodeling. An inhibitor may also have potential use for treatment of mast cell mediated diseases such as dermatitis, asthma, chronic obstructive pulmonary disease (COPD), and pulmonary inflammation, since Chymase is implicated in microvascular leakage, neutrophil accumulation, the stimulation of mucus secretion, and the modulation of cytokines (He et al., Eur. J. Pharmacol., 1998, 352, 91).

Several small molecule Chymase inhibitors have been reported to be efficacious in the cardiomyopathic hamster model of heart failure (Takai et al. J. Pharmacol. Exp. Ther. 2003, 305, 17), in carotid artery injury by a balloon catheter in dogs (Takai et al. J. Pharmacol. Exp. Ther, 2003, 304, 841), and in the hamster left anterior descending coronary artery ligation model of heart failure (WO 03/018061). Additionally, a Chymase inhibitor has been demonstrated to be efficacious in a sheep asthma model (WO 2005/073214). PCT application PCT/US2008/072849 and the present application are commonly owned by the assignee of this application and discloses quinazolinedione useful as Chymase inhibitors.

SUMMARY OF THE INVENTION

It is therefore an object of the invention to provide a small molecule a Chymase inhibitor as defined herein, and pharmaceutical compositions thereof.

It is also an object of the invention to provide methods of using said Chymase inhibitors to treat various diseases and conditions related thereto.

It is a further object of the invention to provide processes of preparing said Chymase inhibitors.

DETAILED DESCRIPTION OF THE INVENTION

In a first generic embodiment, there is provided a compound of the formula (I):

(I)

wherein $X_1$, $X_2$, $X_3$ and $X_4$ are each independently —CH— or nitrogen, with the proviso that at least one of them is nitrogen;

E is —COOH or —COOR wherein R is $C_1$-$C_5$ alkyl;

G is $C_1$-$C_2$ alkyl;

J is a heteroaryl group optionally substituted with 1-3 substituents chosen from halogen, $C_1$-$C_3$ alkyl and $C_1$-$C_3$ alkoxy;

M is $C_1$-$C_5$ alkyl optionally substituted with 1-3 substitutents chosen from $C_1$-$C_5$ alkyl and $C_3$-$C_6$ carbocycle;

or the pharmaceutically acceptable salts thereof.

In another embodiment, there is provided a compound as described herein above and wherein:

E is —COOH or —COOR wherein R is $C_1$-$C_3$ alkyl;

G is —$CH_2$—;

J is a heteroaryl group chosen from indolyl, benzothiazolyl and benzoisothiazolyl each optionally substituted with 1-3 $C_1$-$C_3$ alkyl groups;

M is $C_1$-$C_3$ alkyl optionally substituted with 1-3 substitutents chosen from $C_1$-$C_5$ alkyl, phenyl and cyclopropyl;

In another embodiment, there is provided a compound as described hereinabove and wherein:

E is —COOH;

J is a heteroaryl group chosen from indolyl and benzoisothiazolyl each optionally substituted with 1-3 methyl groups;

M is $C_1$-$C_2$ alkyl optionally substituted with 1-3 substitutents chosen from $C_1$-$C_5$ alkyl, phenyl and cyclopropyl;

In another embodiment, there is provided a compound as described hereinabove and wherein:

-continued

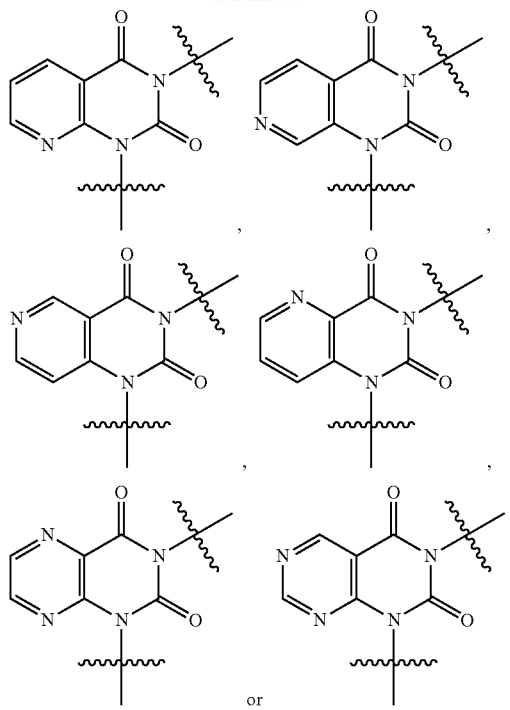

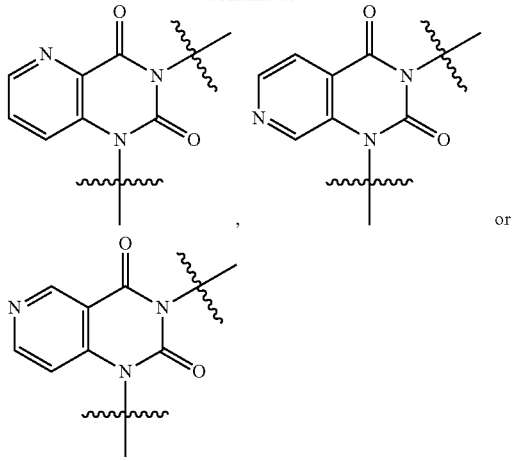

or

J is a heteroaryl group chosen from indolyl or benzoisothiazolyl each optionally substituted with 2-3 methyl groups;

M is $C_1$-$C_2$ alkyl optionally substituted with 1 substitutent chosen from $C_1$-$C_5$ alkyl, phenyl and cyclopropyl;

In another embodiment, there is provided a compound as described hereinabove and wherein:

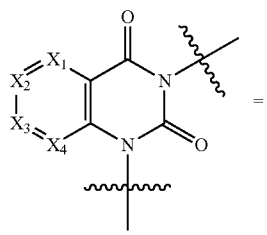

In another embodiment, there is provide a compound as described hereinabove and wherein:

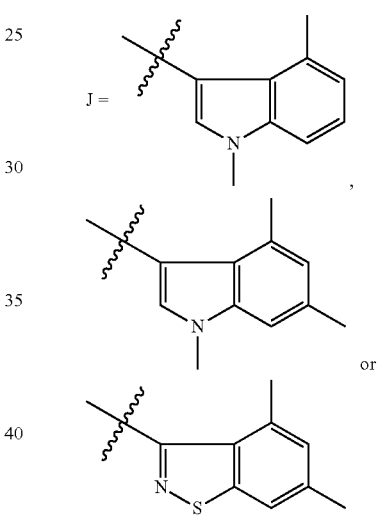

In another embodiment, there is provided compounds of the formula (I) as described in Table I which can be made as described in the schemes and examples herein below, and by methods apparent to those of ordinary skill in the art:

TABLE I

| Structure | Name |
|---|---|
| 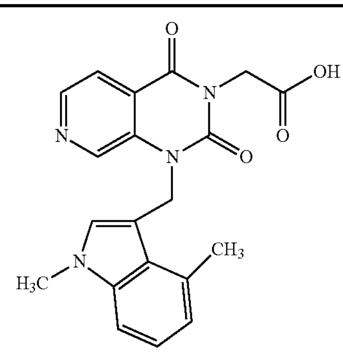 | [1-(1,4-Dimethyl-1H-indol-3-ylmethyl)-2,4-dioxo-1,4-dihydro-2H-pyrido[3,4-d]pyrimidin-3-yl]-acetic acid |

TABLE I-continued

| Structure | Name |
|---|---|
| 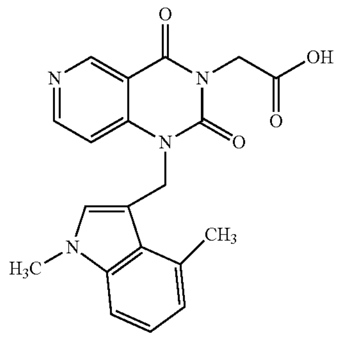 [SMILES: Cc1cccc2c1c(Cn1c(=O)n(CC(=O)O)c(=O)c3cnccc31)cn2C] | [1-(1,4-Dimethyl-1H-indol-3-ylmethyl)-2,4-dioxo-1,4-dihydro-2H-pyrido[4,3-d]pyrimidin-3-yl]-acetic acid |
| 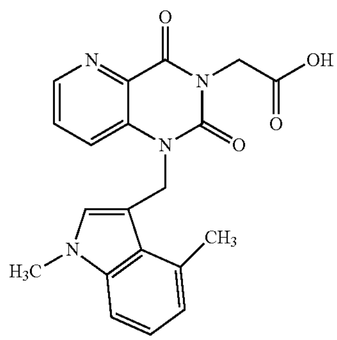 [SMILES: Cc1cccc2c1c(Cn1c(=O)n(CC(=O)O)c(=O)c3ncccc31)cn2C] | [1-(1,4-Dimethyl-1H-indol-3-ylmethyl)-2,4-dioxo-1,4-dihydro-2H-pyrido[3,2-d]pyrimidin-3-yl]-acetic acid |
| 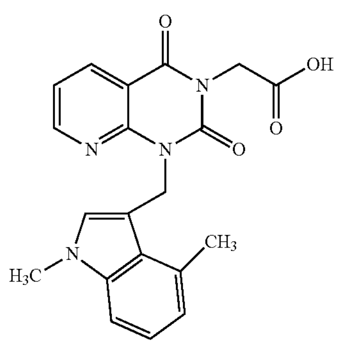 [SMILES: Cc1cccc2c1c(Cn1c(=O)n(CC(=O)O)c(=O)c3cccnc31)cn2C] | [1-(1,4-Dimethyl-1H-indol-3-ylmethyl)-2,4-dioxo-1,4-dihydro-2H-pyrido[2,3-d]pyrimidin-3-yl]-acetic acid |
| 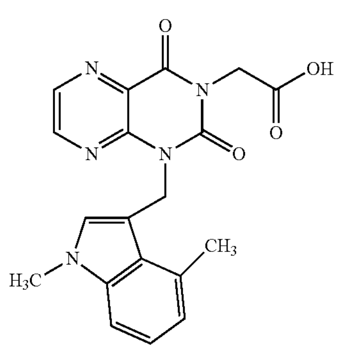 [SMILES: Cc1cccc2c1c(Cn1c(=O)n(CC(=O)O)c(=O)c3nccnc31)cn2C] | [1-(1,4-Dimethyl-1H-indol-3-ylmethyl)-2,4-dioxo-1,4-dihydro-2H-pteridin-3-yl]-acetic acid |

TABLE I-continued

| Structure | Name |
|---|---|
| 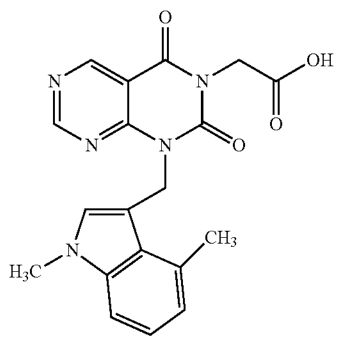 [SMILES: Cc1cccc2c1c(Cn1c(=O)n(CC(=O)O)c(=O)c3cncnc31)cn2C] | [1-(1,4-Dimethyl-1H-indol-3-ylmethyl)-2,4-dioxo-1,4-dihydro-2H-pyrimido[4,5-d]pyrimidin-3-yl]-acetic acid |
| Chiral | (S)-[1-(1,4-Dimethyl-1H-indol-3-ylmethyl)-2,4-dioxo-1,4-dihydro-2H-pyrido[4,3-d]pyrimidin-3-yl]-phenyl-acetic acid |
| Chiral | (R)-3-[1-(1,4-Dimethyl-1H-indol-3-ylmethyl)-2,4-dioxo-1,4-dihydro-2H-pyrido[4,3-d]pyrimidin-3-yl]-3-phenyl-propionic acid ethyl ester |
| 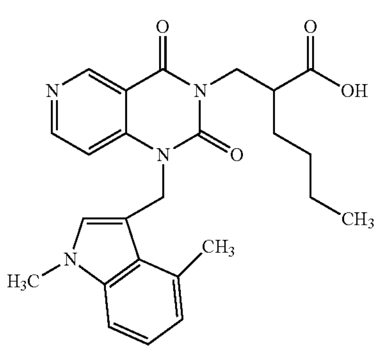 [SMILES: CCCCC(Cn1c(=O)c2cnccc2n(Cc2cn(C)c3cccc(C)c23)c1=O)C(=O)O] | 2-[1-(1,4-Dimethyl-1H-indol-3-ylmethyl)-2,4-dioxo-1,4-dihydro-2H-pyrido[4,3-d]pyrimidin-3-ylmethyl]-hexanoic aci |

TABLE I-continued

| Structure | | Name |
|---|---|---|
| (structure) | Chiral | (S)-3-[1-(4,6-Dimethyl-benzo[d]isothiazol-3-ylmethyl)-2,4-dioxo-1,4-dihydro-2H-pyrido[3,2-d]pyrimidin-3-yl]-pentanoic acid |
| (structure) | Chiral | (S)-3-[1-(4,6-Dimethyl-benzo[d]isothiazol-3-ylmethyl)-2,4-dioxo-1,4-dihydro-2H-pyrido[4,3-d]pyrimidin-3-yl]-pentanoic acid |
| (structure) | Chiral | (S)-2-[1-(4,6-Dimethyl-benzo[d]isothiazol-3-ylmethyl)-2,4-dioxo-1,4-dihydro-2H-pyrido[4,3-d]pyrimidin-3-yl]-butyric acid |

TABLE I-continued

| Structure | | Name |
|---|---|---|
| (structure) | Chiral | (R)-2-[1-(4,6-Dimethyl-benzo[d]isothiazol-3-ylmethyl)-2,4-dioxo-1,4-dihydro-2H-pyrido[4,3-d]pyrimidin-3-yl]-hexanoic acid |
| (structure) | Chiral | (S)-2-[1-(4,6-Dimethyl-benzo[d]isothiazol-3-ylmethyl)-2,4-dioxo-1,4-dihydro-2H-pyrido[4,3-d]pyrimidin-3-yl]-hexanoic acid |
| (structure) | Chiral | (S)-2-[1-(1,4-Dimethyl-1H-indol-3-ylmethyl)-2,4-dioxo-1,4-dihydro-2H-pyrido[4,3-d]pyrimidin-3-yl]-pentanoic acid |

TABLE I-continued
| Structure | Name |
|---|---|
| 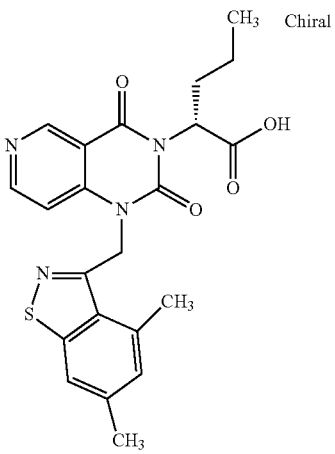 [SMILES: CCC[C@H](C(=O)O)n1c(=O)c2cnccc2n(Cc2nsc3cc(C)cc(C)c23)c1=O] | (R)-2-[1-(4,6-Dimethyl-benzo[d]isothiazol-3-ylmethyl)-2,4-dioxo-1,4-dihydro-2H-pyrido[4,3-d]pyrimidin-3-yl]-pentanoic acid |
| 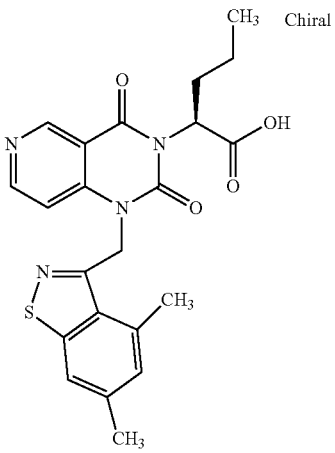 [SMILES: CCC[C@@H](C(=O)O)n1c(=O)c2cnccc2n(Cc2nsc3cc(C)cc(C)c23)c1=O] | (S)-2-[1-(4,6-Dimethyl-benzo[d]isothiazol-3-ylmethyl)-2,4-dioxo-1,4-dihydro-2H-pyrido[4,3-d]pyrimidin-3-yl]-pentanoic acid |
| 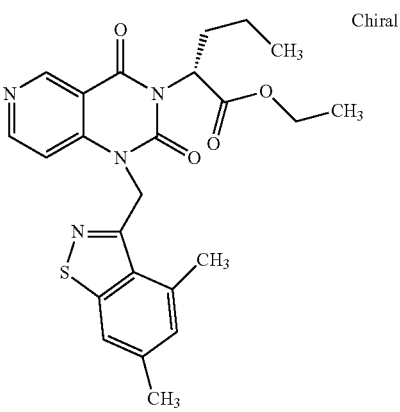 [SMILES: CCC[C@H](C(=O)OCC)n1c(=O)c2cnccc2n(Cc2nsc3cc(C)cc(C)c23)c1=O] | (R)-2-[1-(4,6-Dimethyl-benzo[d]isothiazol-3-ylmethyl)-2,4-dioxo-1,4-dihydro-2H-pyrido[4,3-d]pyrimidin-3-yl]-pentanoic acid ethyl ester |

TABLE I-continued

| Structure | Name |
|---|---|
| | (R)-2-[1-(1,4-Dimethyl-1H-indol-3-ylmethyl)-2,4-dioxo-1,4-dihydro-2H-pyrido[4,3-d]pyrimidin-3-yl]-hexanoic acid |
| | (R)-3-[1-(1,4-Dimethyl-1H-indol-3-ylmethyl)-2,4-dioxo-1,4-dihydro-2H-pyrido[4,3-d]pyrimidin-3-yl]-pentanoic acid |
| | (R)-3-[1-(1,4-Dimethyl-1H-indol-3-ylmethyl)-2,4-dioxo-1,4-dihydro-2H-pyrido[3,4-d]pyrimidin-3-yl]-pentanoic acid |
| | (S)-3-[1-(1,4-Dimethyl-1H-indol-3-ylmethyl)-2,4-dioxo-1,4-dihydro-2H-pyrido[3,2-d]pyrimidin-3-yl]-pentanoic acid |

TABLE I-continued

| Structure | Name |
|---|---|
| | (R)-3-[1-(4,6-Dimethyl-benzo[d]isothiazol-3-ylmethyl)-2,4-dioxo-1,4-dihydro-2H-pyrido[3,4-d]pyrimidin-3-yl]-pentanoic acid |
| | (R)-3-[1-(4,6-Dimethyl-benzo[d]isothiazol-3-ylmethyl)-2,4-dioxo-1,4-dihydro-2H-pyrido[4,3-d]pyrimidin-3-yl]-pentanoic acid |
| | (R)-3-[1-(1,4-Dimethyl-1H-indol-3-ylmethyl)-2,4-dioxo-1,4-dihydro-2H-pyrido[3,2-d]pyrimidin-3-yl]-pentanoic acid |
| | (R)-3-[1-(4,6-Dimethyl-benzo[d]isothiazol-3-ylmethyl)-2,4-dioxo-1,4-dihydro-2H-pyrido[3,2-d]pyrimidin-3-yl]-pentanoic acid |

TABLE I-continued
| Structure | | Name |
|---|---|---|
| 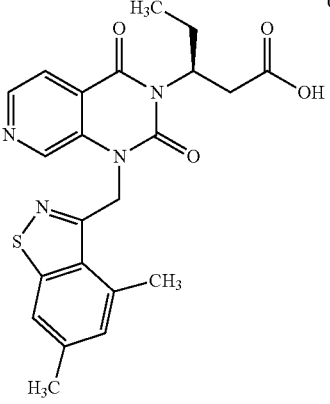 | Chiral | (S)-3-[1-(4,6-Dimethyl-benzo[d]isothiazol-3-ylmethyl)-2,4-dioxo-1,4-dihydro-2H-pyrido[3,4-d]pyrimidin-3-yl]-pentanoic acid |
| 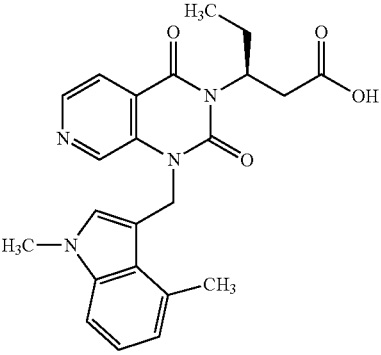 | Chiral | (S)-3-[1-(1,4-Dimethyl-1H-indol-3-ylmethyl)-2,4-dioxo-1,4-dihydro-2H-pyrido[3,4-d]pyrimidin-3-yl]-pentanoic acid |
| 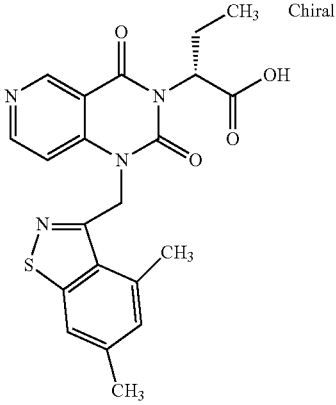 [SMILES: CC[C@H](C(=O)O)n1c(=O)c2cnccc2n(Cc2nsc3cc(C)cc(C)c23)c1=O] | Chiral | (R)-2-[1-(4,6-Dimethyl-benzo[d]isothiazol-3-ylmethyl)-2,4-dioxo-1,4-dihydro-2H-pyrido[4,3-d]pyrimidin-3-yl]-butyric acid |

TABLE I-continued

| Structure | Name |
|---|---|
| | 3-Cyclopropyl-3-[2,4-dioxo-1-(1,4,6-trimethyl-1H-indol-3-ylmethyl)-1,4-dihydro-2H-pyrido[3,2-d]pyrimidin-3-yl]-propionic acid |
| Chiral | (R)-3-[2,4-Dioxo-1-(1,4,6-trimethyl-1H-indol-3-ylmethyl)-1,4-dihydro-2H-pyrido[3,2-d]pyrimidin-3-yl]-pentanoic acid |
| Chiral | (S)-2-[1-(4,6-Dimethyl-benzo[d]isothiazol-3-ylmethyl)-2,4-dioxo-1,4-dihydro-2H-pyrido[3,2-d]pyrimidin-3-yl]-butyric acid |

TABLE I-continued
| Structure | Name |
|---|---|
| 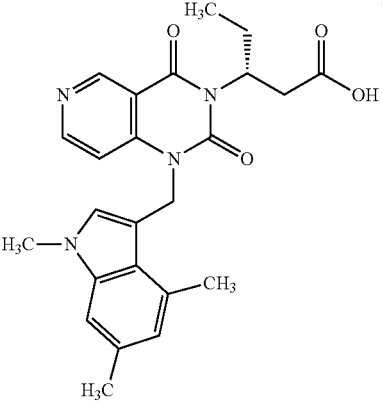 | Chiral (R)-3-[2,4-Dioxo-1-(1,4,6-trimethyl-1H-indol-3-ylmethyl)-1,4-dihydro-2H-pyrido[4,3-d]pyrimidin-3-yl]-pentanoic acid |
| 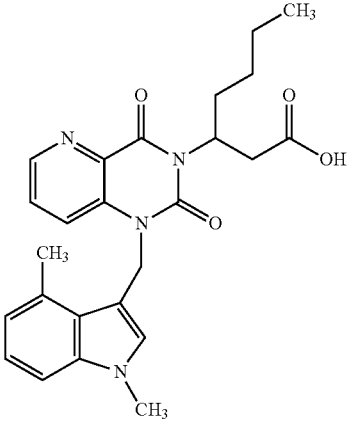 [SMILES: CCCCC(CC(=O)O)n1c(=O)c2ncccc2n(Cc2cn(C)c3cccc(C)c23)c1=O] | 3-[1-(1,4-Dimethyl-1H-indol-3-ylmethyl)-2,4-dioxo-1,4-dihydro-2H-pyrido[3,2-d]pyrimidin-3-yl]-heptanoic acid |
| 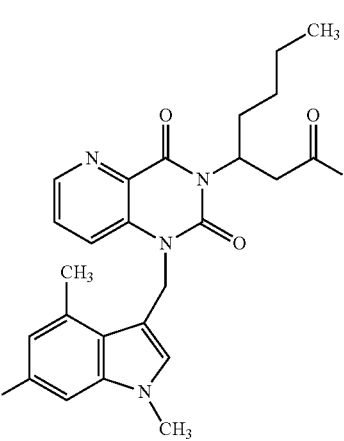 | 3-[2,4-Dioxo-1-(1,4,6-trimethyl-1H-indol-3-ylmethyl)-1,4-dihydro-2H-pyrido[3,2-d]pyrimidin-3-yl]-heptanoic acid |

TABLE I-continued

| Structure | Name |
|---|---|
|  | 3-[1-(1,4-Dimethyl-1H-indol-3-ylmethyl)-2,4-dioxo-1,4-dihydro-2H-pyrido[3,2-d]pyrimidin-3-yl]-hexanoic acid | or a pharmaceutically acceptable salt thereof.

The following is Chymase IC50 (nM) data for preferred formula (I) compounds of the invention:

TABLE II

| Compounds | Chymase IC50 (nM) |
|---|---|
| [1-(1,4-Dimethyl-1H-indol-3-ylmethyl)-2,4-dioxo-1,4-dihydro-2H-pyrido[3,4-d]pyrimidin-3-yl]-acetic acid | 36 |
| [1-(1,4-Dimethyl-1H-indol-3-ylmethyl)-2,4-dioxo-1,4-dihydro-2H-pyrido[4,3-d]pyrimidin-3-yl]-acetic acid | 9.6 |
| [1-(1,4-Dimethyl-1H-indol-3-ylmethyl)-2,4-dioxo-1,4-dihydro-2H-pyrido[3,2-d]pyrimidin-3-yl]-acetic acid | 6.1 |
| (S)-[1-(1,4-Dimethyl-1H-indol-3-ylmethyl)-2,4-dioxo-1,4-dihydro-2H-pyrido[4,3-d]pyrimidin-3-yl]-phenyl-acetic acid | 3.1 |
| 2-[1-(1,4-Dimethyl-1H-indol-3-ylmethyl)-2,4-dioxo-1,4-dihydro-2H-pyrido[4,3-d]pyrimidin-3-ylmethyl]-hexanoic aci | 11 |
| (S)-3-[1-(4,6-Dimethyl-benzo[d]isothiazol-3-ylmethyl)-2,4-dioxo-1,4-dihydro-2H-pyrido[3,2-d]pyrimidin-3-yl]-pentanoic acid | 8 |
| (S)-3-[1-(4,6-Dimethyl-benzo[d]isothiazol-3-ylmethyl)-2,4-dioxo-1,4-dihydro-2H-pyrido[4,3-d]pyrimidin-3-yl]-pentanoic acid | 17 |
| (S)-2-[1-(4,6-Dimethyl-benzo[d]isothiazol-3-ylmethyl)-2,4-dioxo-1,4-dihydro-2H-pyrido[4,3-d]pyrimidin-3-yl]-butyric acid | 7 |
| (R)-2-[1-(4,6-Dimethyl-benzo[d]isothiazol-3-ylmethyl)-2,4-dioxo-1,4-dihydro-2H-pyrido[4,3-d]pyrimidin-3-yl]-hexanoic acid | 2.6 |
| (S)-2-[1-(4,6-Dimethyl-benzo[d]isothiazol-3-ylmethyl)-2,4-dioxo-1,4-dihydro-2H-pyrido[4,3-d]pyrimidin-3-yl]-hexanoic acid | 7 |
| (S)-2-[1-(1,4-Dimethyl-1H-indol-3-ylmethyl)-2,4-dioxo-1,4-dihydro-2H-pyrido[4,3-d]pyrimidin-3-yl]-pentanoic acid | 2.1 |
| (R)-2-[1-(4,6-Dimethyl-benzo[d]isothiazol-3-ylmethyl)-2,4-dioxo-1,4-dihydro-2H-pyrido[4,3-d]pyrimidin-3-yl]-pentanoic acid | 4 |
| (S)-2-[1-(4,6-Dimethyl-benzo[d]isothiazol-3-ylmethyl)-2,4-dioxo-1,4-dihydro-2H-pyrido[4,3-d]pyrimidin-3-yl]-pentanoic acid | 4.8 |
| (R)-2-[1-(1,4-Dimethyl-1H-indol-3-ylmethyl)-2,4-dioxo-1,4-dihydro-2H-pyrido[4,3-d]pyrimidin-3-yl]-hexanoic acid | 0.9 |
| (R)-3-[1-(1,4-Dimethyl-1H-indol-3-ylmethyl)-2,4-dioxo-1,4-dihydro-2H-pyrido[4,3-d]pyrimidin-3-yl]-pentanoic acid | 2.5 |
| (R)-3-[1-(1,4-Dimethyl-1H-indol-3-ylmethyl)-2,4-dioxo-1,4-dihydro-2H-pyrido[3,4-d]pyrimidin-3-yl]-pentanoic acid | 6.1 |
| (S)-3-[1-(1,4-Dimethyl-1H-indol-3-ylmethyl)-2,4-dioxo-1,4-dihydro-2H-pyrido[3,2-d]pyrimidin-3-yl]-pentanoic acid | 3 |
| (R)-3-[1-(4,6-Dimethyl-benzo[d]isothiazol-3-ylmethyl)-2,4-dioxo-1,4-dihydro-2H-pyrido[3,4-d]pyrimidin-3-yl]-pentanoic acid | 20 |
| (R)-3-[1-(4,6-Dimethyl-benzo[d]isothiazol-3-ylmethyl)-2,4-dioxo-1,4-dihydro-2H-pyrido[4,3-d]pyrimidin-3-yl]-pentanoic acid | 9.9 |
| (R)-3-[1-(1,4-Dimethyl-1H-indol-3-ylmethyl)-2,4-dioxo-1,4-dihydro-2H-pyrido[3,2-d]pyrimidin-3-yl]-pentanoic acid | 1.4 |
| (R)-3-[1-(4,6-Dimethyl-benzo[d]isothiazol-3-ylmethyl)-2,4-dioxo-1,4-dihydro-2H-pyrido[3,2-d]pyrimidin-3-yl]-pentanoic acid | 2.2 |
| (S)-3-[1-(4,6-Dimethyl-benzo[d]isothiazol-3-ylmethyl)-2,4-dioxo-1,4-dihydro-2H-pyrido[3,4-d]pyrimidin-3-yl]-pentanoic acid | 27 |
| (S)-3-[1-(1,4-Dimethyl-1H-indol-3-ylmethyl)-2,4-dioxo-1,4-dihydro-2H-pyrido[3,4-d]pyrimidin-3-yl]-pentanoic acid | 7.4 |
| (R)-2-[1-(4,6-Dimethyl-benzo[d]isothiazol-3-ylmethyl)-2,4-dioxo-1,4-dihydro-2H-pyrido[4,3-d]pyrimidin-3-yl]-butyric acid | 2.6 |
| 3-Cyclopropyl-3-[2,4-dioxo-1-(1,4,6-trimethyl-1H-indol-3-ylmethyl)-1,4-dihydro-2H-pyrido[3,2-d]pyrimidin-3-yl]-propionic acid | 0.7 |
| (R)-3-[2,4-Dioxo-1-(1,4,6-trimethyl-1H-indol-3-ylmethyl)-1,4-dihydro-2H-pyrido[3,2-d]pyrimidin-3-yl]-pentanoic acid | 0.4 |
| (S)-2-[1-(4,6-Dimethyl-benzo[d]isothiazol-3-ylmethyl)-2,4-dioxo-1,4-dihydro-2H-pyrido[3,2-d]pyrimidin-3-yl]-butyric acid | 2.7 |
| (R)-3-[2,4-Dioxo-1-(1,4,6-trimethyl-1H-indol-3-ylmethyl)-1,4-dihydro-2H-pyrido[4,3-d]pyrimidin-3-yl]-pentanoic acid | 0.7 |
| 3-[1-(1,4-Dimethyl-1H-indol-3-ylmethyl)-2,4-dioxo-1,4-dihydro-2H-pyrido[3,2-d]pyrimidin-3-yl]-heptanoic acid | 1.4 |
| 3-[2,4-Dioxo-1-(1,4,6-trimethyl-1H-indol-3-ylmethyl)-1,4-dihydro-2H-pyrido[3,2-d]pyrimidin-3-yl]-heptanoic acid | 0.3 |
| 3-[1-(1,4-Dimethyl-1H-indol-3-ylmethyl)-2,4-dioxo-1,4-dihydro-2H-pyrido[3,2-d]pyrimidin-3-yl]-hexanoic acid | 1.3 |

In all the compounds disclosed hereinabove in this application, in the event the nomenclature is in conflict with the structure, it shall be understood that the compound is defined by the structure.

The invention includes the use of any compounds of described above containing one or more asymmetric carbon atoms may occur as racemates and racemic mixtures, single enantiomers, diastereomeric mixtures, and individual diastereomers. All such isomeric forms of these compounds are expressly included in the present invention. Each stereogenic carbon may be in the R or S configuration, or a combination of configurations.

Some of the compounds of formula (I) can exist in more than one tautomeric form. The invention includes methods using all such tautomers.

All terms as used herein in this specification, unless otherwise stated, shall be understood in their ordinary meaning as known in the art. For example, $C_{1-4}$alkoxy includes the organic radical $C_{1-4}$alkyl with a terminal oxygen, such as methoxy, ethoxy, propoxy, butoxy.

All organic radicals: alkyl, alkenyl and alkynyl groups, or such groups which are incorporated in other radicals such as acyl and alkoxy, shall be understood as being branched or unbranched where structurally possible and unless otherwise specified, and may be partially or fully halogenated.

The term "lower" referred to above and hereinafter in connection with organic radicals or compounds respectively defines such as branched or unbranched with up to and including 7, preferably up to and including 4 and advantageously one or two carbon atoms.

A cyclic group shall be understood to mean carbocycle, heterocycle or heteroaryl, each may be partially or fully halogenated.

Carbocycles include hydrocarbon rings containing from three to fourteen carbon atoms. These carbocycles may be either aromatic either aromatic or non-aromatic ring systems. The non-aromatic ring systems may be mono- or polyunsaturated, monocyclic, bicyclic or tricyclic and may be bridged. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, benzyl, indanyl, indenyl, benzocyclobutanyl, dihydronaphthyl, tetrahydronaphthyl, naphthyl, decahydronaphthyl, benzocycloheptanyl, adamantyl, norbornyl, fluorene, and benzocycloheptenyl. Certain terms for cycloalkyl such as cyclobutanyl and cyclobutyl shall be used interchangeably. Carbocycles shall be understood where structurally possible to be optionally partially or fully halogenated.

The term "heterocycle" refers to a stable nonaromatic 4-8 membered (but preferably, 5 or 6 membered) monocyclic or non-aromatic 8-11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure. Unless otherwise stated, heterocycles include but are not limited to, for example pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, tetrahydropyranyl, tetrahydrofuranyl, 1,3-dioxolanone, 1,3-dioxanone, 1,4-dioxanyl, piperidinonyl, tetrahydropyrimidonyl, pentamethylene sulfide, pentamethylene sulfoxide, pentamethylene sulfone, tetramethylene sulfide, tetramethylene sulfoxide and tetramethylene sulfone.

The term "heteroaryl" shall be understood to mean an aromatic 5-6 membered monocyclic or 7-10 membered bicyclic ring containing 1-4 heteroatoms such as N, O and S. Unless otherwise stated, such heteroaryls include aziridinyl, thienyl, furanyl, isoxazolyl, oxazolyl, thiazolyl, thiadiazolyl, pyrazolyl, pyrrolyl, imidazolyl, pyridinyl, pyrimidinyl, pyrazinyl, pyridazinyl, pyranyl, indolyl, azaindolyl, isoindolyl, benzoxazolyl, benzothiazolyl, benzisothiazolyl, benzimidazolyl, isoquinolinyl, quinolinyl, benzofuranyl, benzodioxolyl, indazolyl or triazolyl.

The term "heteroatom" as used herein shall be understood to mean atoms other than carbon such as oxygen, nitrogen, sulfur and phosphorous.

As used herein, "nitrogen" and "sulfur" include any oxidized form of nitrogen and sulfur and the quaternized form of any basic nitrogen. All heteroatoms in open chain or cyclic radicals include all oxidized forms.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein shall be understood to mean aromatic carbocycle or heteroaryl as defined herein. Each aryl or heteroaryl unless otherwise specified includes it's partially or fully hydrogenated derivative and/or is partially or fully halogenated. For example, quinolinyl may include decahydroquinolinyl and tetrahydroquinolinyl, naphthyl may include its hydrogenated derivatives such as tetrahydranaphthyl. Other partially or fully hydrogenated derivatives of the aryl and heteroaryl compounds described herein will be apparent to one of ordinary skill in the art.

The term "halogen" as used in the present specification shall be understood to mean bromine, chlorine, fluorine or iodine, preferably fluorine. The definitions "partially or fully halogenated"; partially or fully fluorinated; "substituted by one or more halogen atoms", includes for example, mono, di or tri halo derivatives on one or more carbon atoms. For alkyl, a nonlimiting example would be —$CH_2CHF_2$, —$CF_3$ etc.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—($C_1$-$C_4$ alkyl)$_4^+$ salts.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds described herein are either commercially available or can be made by methods and any necessary intermediates well known in the art.

In order that this invention be more fully understood, the following examples are set forth. These examples are for the purpose of illustrating preferred embodiments of this invention, and are not to be construed as limiting the scope of the invention in any way.

The examples which follow are illustrative and, as recognized by one skilled in the art, particular reagents or conditions could be modified as needed for individual compounds without undue experimentation. Starting materials used in the scheme below are either commercially available or easily prepared from commercially available materials by those skilled in the art.

General Synthetic Methods

The invention also provides processes for making compounds of Formula (I). In the scheme, unless specified otherwise, $X_1$, $X_2$, $X_3$, $X_4$, E, G, J and M in the formulas below shall have the meaning of $X_1$, $X_2$, $X_3$, $X_4$, E, G, J and M in Formula (I) of the invention described herein above.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC), if desired, and intermediates and products may be purified by chromatography on silica gel and/or by recrystallization.

The appropriately substituted starting materials and intermediates used in the preparation of compounds of the invention are either commercially available or readily prepared by methods known in the literature to those skilled in the art, and are illustrated in the synthetic examples below.

Compounds of Formula (I) may be synthesized by the method illustrated in Scheme 1.

Scheme 1

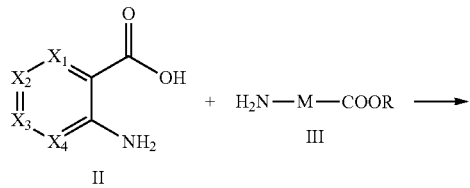

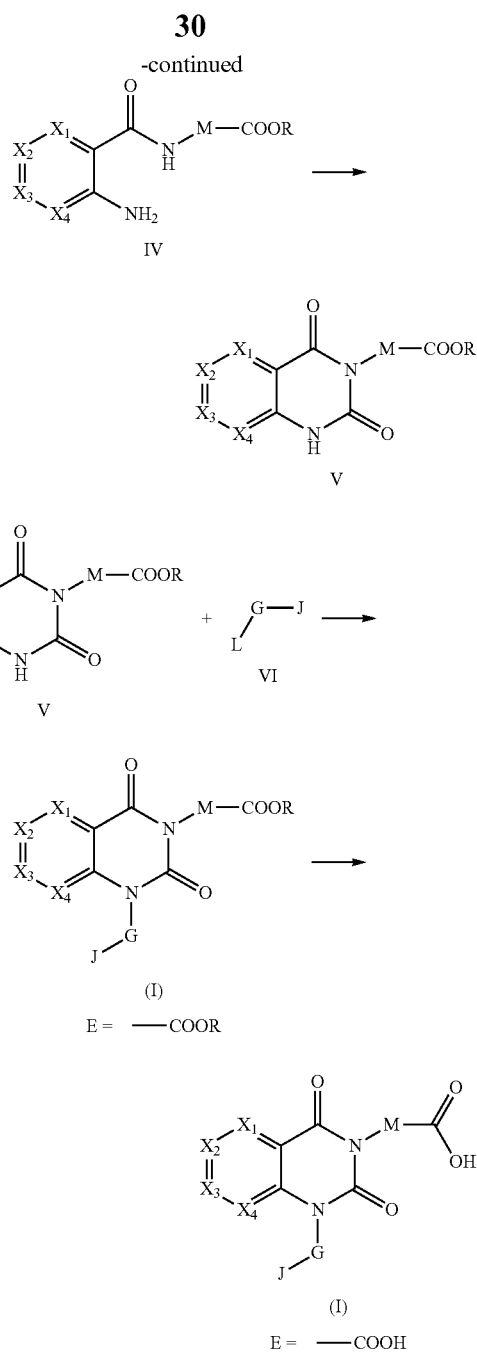

As illustrated in Scheme 1, reaction of an acid of formula (II) with an amine of formula (III), in a suitable solvent, under standard coupling conditions, provides an amide of formula (IV) wherein R═$C_1$-$C_5$ alkyl. Cyclization of the intermediate of formula (IV) with reagents such as carbonyldiimidazole and DBU, in a suitable solvent, provides the quinazoline dione of formula (V). Alkylation of the intermediate of formula (V) with an alkylating agent L-G-J (VI), wherein L=leaving group such as halogen, ammonium salt etc., in a suitable solvent and base, provides the alkylated compound of Formula (I) where E═—COOR. Hydrolysis of the ester provides another compound of Formula (I) wherein E═—COOH.

Further modification of the initial product of Formula (I) by methods known to one skilled in the art and illustrated in the examples below, provides additional compounds of this invention.

EXAMPLES

Example 1

Synthesis of [1-(1,4-dimethyl-1H-indol-3-ylmethyl)-2,4-dioxo-1,4-dihydro-2H-pyrido[3,4-d]pyrimidin-3-yl]-acetic acid

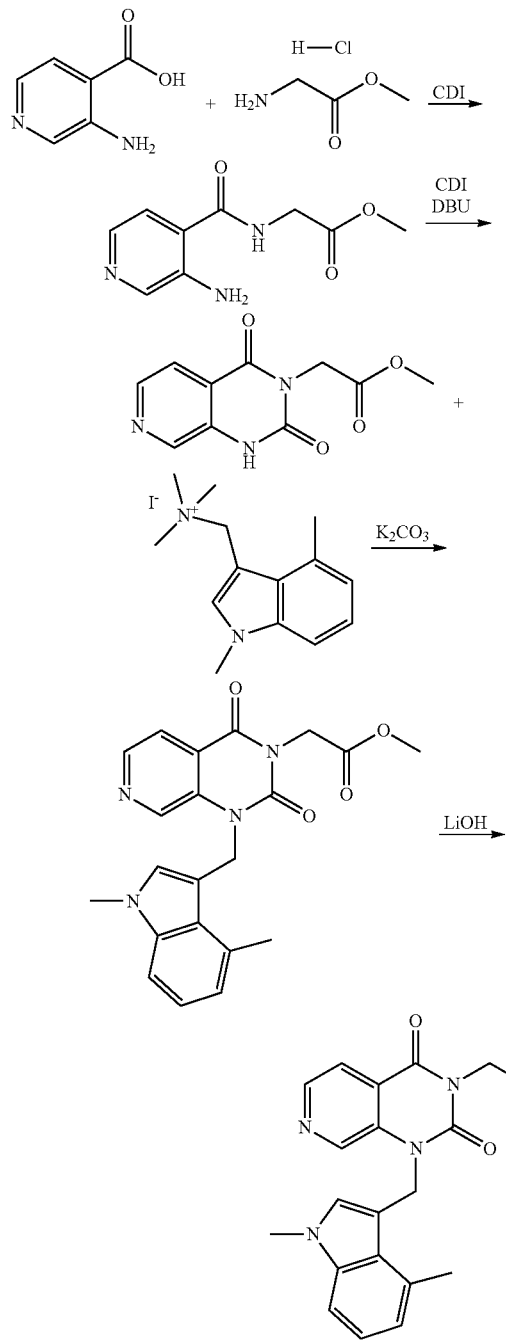

To a solution of 100 mg of 3-amino-isonicotinic acid in pyridine (2.5 mL) is added 117 mg of 1,1'-carbonyldiimidazole and the mixture is stirred for 20 min at 55° C. Then the mixture is cooled to room temperature and 91 mg of glycine methylester hydrochloride is added and the resulting mixture is stirred for 30 min at 55° C. and 1 h at room temperature. Then the solvent is removed under vacuum and the residue is purified by flash chromatography on silica gel to give 100 mg (66%) of [(3-amino-pyridine-4-carbonyl)-amino]-acetic acid methyl ester.

To a solution of 100 mg of [(3-amino-pyridine-4-carbonyl)-amino]-acetic acid methyl ester in tetrahydrofuran (4.5 mL) is added 194 mg of 1,1'-carbonyldiimidazole and 0.18 mL of 1,8-diazabicyclo[5.4.0]undec-7-ene at room temperature and the mixture is stirred at the same temperature for 2 h. Then the solvent is removed under vacuum and the residue is purified by flash chromatography on silica gel to give 100 mg (89%) of (2,4-dioxo-1,4-dihydro-2H-pyrido[3,4-d]pyrimidin-3-yl)-acetic acid methyl ester.

To a solution of 62 mg of (2,4-dioxo-1,4-dihydro-2H-pyrido[3,4-d]pyrimidin-3-yl)-acetic acid methyl ester in N,N-dimethylformamide (2.5 mL) is added 109 mg of (1,4-dimethyl-1H-indol-3-ylmethyl)-trimethylammonium iodide and 44 mg of potassium carbonate at room temperature. The solution is heated to 60° C. for 2.5 h. Then the reaction is cooled to room temperature and stirred for another 16 hrs. Then 50 mL of water is added and a pale yellow solid is formed. The solid is collected and rinsed with water. Purification of this solid by flash chromatography on silica gel gives 98 mg (95%) of [1-(1,4-dimethyl-1H-indol-3-ylmethyl)-2,4-dioxo-1,4-dihydro-2H-pyrido[3,4-d]pyrimidin-3-yl]-acetic acid methyl ester.

To a solution of 70 mg of [1-(1,4-dimethyl-1H-indol-3-ylmethyl)-2,4-dioxo-1,4-dihydro-2H-pyrido[3,4-d]pyrimidin-3-yl]-acetic acid methyl ester in 1,4-dioxane (2.0 mL) is added lithium hydroxide solution (11 mg of lithium hydroxide monohydrate in 0.5 mL of water) at room temperature. The solution is stirred at the same temperature for 5 h. Then 1.0 mL of 1.0 M hydrochloric acid is added along with 50 mL of water. The mixture is extracted with ethyl acetate (3×50 mL) and the organic layers are combined, dried over magnesium sulfate and concentrated to give crude product. The crude product is rinsed with methanol (3.0 mL) and dichloromethane (5.0 mL) and the remaining light yellow solid is dried to give 45 mg (67%) of [1-(1,4-dimethyl-1H-indol-3-ylmethyl)-2,4-dioxo-1,4-dihydro-2H-pyrido[3,4-d]pyrimidin-3-yl]-acetic acid; LCMS (ESMS): m/z 379.16 (M+H$^+$).

The following compounds are synthesized using a similar procedure.

[1-(1,4-Dimethyl-1H-indol-3-ylmethyl)-2,4-dioxo-1,4-dihydro-2H-pyrido[4,3-d]pyrimidin-3-yl]-acetic acid; LCMS (ESMS): m/z 379 (M+H$^+$)

[1-(1,4-Dimethyl-1H-indol-3-ylmethyl)-2,4-dioxo-1,4-dihydro-2H-pyrido[3,2-d]pyrimidin-3-yl]-acetic acid; LCMS (ESMS): m/z 379 (M+H$^+$)

[1-(1,4-Dimethyl-1H-indol-3-ylmethyl)-2,4-dioxo-1,4-dihydro-2H-pyrido[2,3-d]pyrimidin-3-yl]-acetic acid; LCMS (ESMS): m/z 379 (M+H$^+$)

[1-(1,4-Dimethyl-1H-indol-3-ylmethyl)-2,4-dioxo-1,4-dihydro-2H-pteridin-3-yl]-acetic acid; LCMS (ESMS): m/z 380 (M+H$^+$)

[1-(1,4-Dimethyl-1H-indol-3-ylmethyl)-2,4-dioxo-1,4-dihydro-2H-pyrimido[4,5-d]pyrimidin-3-yl]-acetic acid; LCMS (ESMS): m/z 380 (M+H$^+$)

(S)-[1-(1,4-Dimethyl-1H-indol-3-ylmethyl)-2,4-dioxo-1,4-dihydro-2H-pyrido[4,3-d]pyrimidin-3-yl]-phenyl-acetic acid; LCMS (ESMS): m/z 455 (M+H$^+$)

(R)-3-[1-(1,4-Dimethyl-1H-indol-3-ylmethyl)-2,4-dioxo-1,4-dihydro-2H-pyrido[4,3-d]pyrimidin-3-yl]-3-phenyl-propionic acid ethyl ester; LCMS (ESMS): m/z 497 (M+H$^+$) (Steps 1-3)

2-[1-(1,4-Dimethyl-1H-indol-3-ylmethyl)-2,4-dioxo-1,4-dihydro-2H-pyrido[4,3-d]pyrimidin-3-ylmethyl]-hexanoic acid; LCMS (ESMS): m/z 449 (M+H$^+$)

(S)-2-[1-(1,4-Dimethyl-1H-indol-3-ylmethyl)-2,4-dioxo-1,4-dihydro-2H-pyrido[4,3-d]pyrimidin-3-yl]-pentanoic acid; LCMS (ESMS): m/z 421 (M+H$^+$)

(R)-2-[1-(1,4-Dimethyl-1H-indol-3-ylmethyl)-2,4-dioxo-1,4-dihydro-2H-pyrido[4,3-d]pyrimidin-3-yl]-hexanoic acid; LCMS (ESMS): m/z 435 (M+H$^+$)

(R)-3-[1-(1,4-Dimethyl-1H-indol-3-ylmethyl)-2,4-dioxo-1,4-dihydro-2H-pyrido[4,3-d]pyrimidin-3-yl]-pentanoic acid; LCMS (ESMS): m/z 421 (M+H$^+$)

(R)-3-[1-(1,4-Dimethyl-1H-indol-3-ylmethyl)-2,4-dioxo-1,4-dihydro-2H-pyrido[3,4-d]pyrimidin-3-yl]-pentanoic acid; LCMS (ESMS): m/z 421 (M+H$^+$)

(S)-3-[1-(1,4-Dimethyl-1H-indol-3-ylmethyl)-2,4-dioxo-1,4-dihydro-2H-pyrido[3,2-d]pyrimidin-3-yl]-pentanoic acid; LCMS (ESMS): m/z 421 (M+H$^+$)

(R)-3-[1-(1,4-Dimethyl-1H-indol-3-ylmethyl)-2,4-dioxo-1,4-dihydro-2H-pyrido[3,2-d]pyrimidin-3-yl]-pentanoic acid; LCMS (ESMS): m/z 421 (M+H$^+$)

(S)-3-[1-(1,4-Dimethyl-1H-indol-3-ylmethyl)-2,4-dioxo-1,4-dihydro-2H-pyrido[3,4-d]pyrimidin-3-yl]-pentanoic acid; LCMS (ESMS): m/z 421 (M+H$^+$)

3-[1-(1,4-Dimethyl-1H-indol-3-ylmethyl)-2,4-dioxo-1,4-dihydro-2H-pyrido[3,2-d]pyrimidin-3-yl]-heptanoic acid; LCMS (ESMS): m/z 449 (M+H$^+$)

3-[1-(1,4-Dimethyl-1H-indol-3-ylmethyl)-2,4-dioxo-1,4-dihydro-2H-pyrido[3,2-d]pyrimidin-3-yl]-hexanoic acid; LCMS (ESMS): m/z 435 (M+H$^+$)

Example 2

Synthesis of (S)-3-[1-(4,6-dimethyl-benzo[d]isothiazol-3-ylmethyl)-2,4-dioxo-1,4-dihydro-2H-pyrido[3,2-d]pyrimidin-3-yl]-pentanoic acid

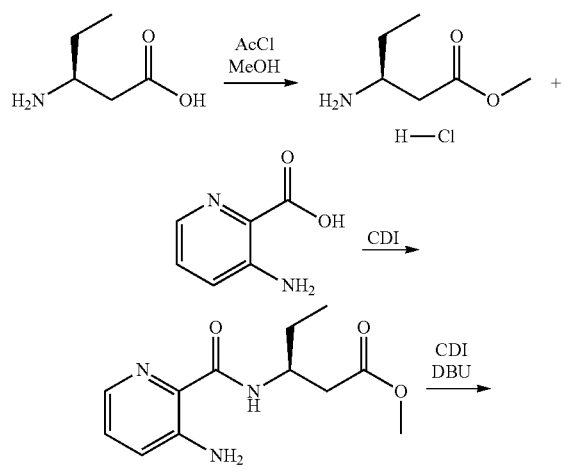

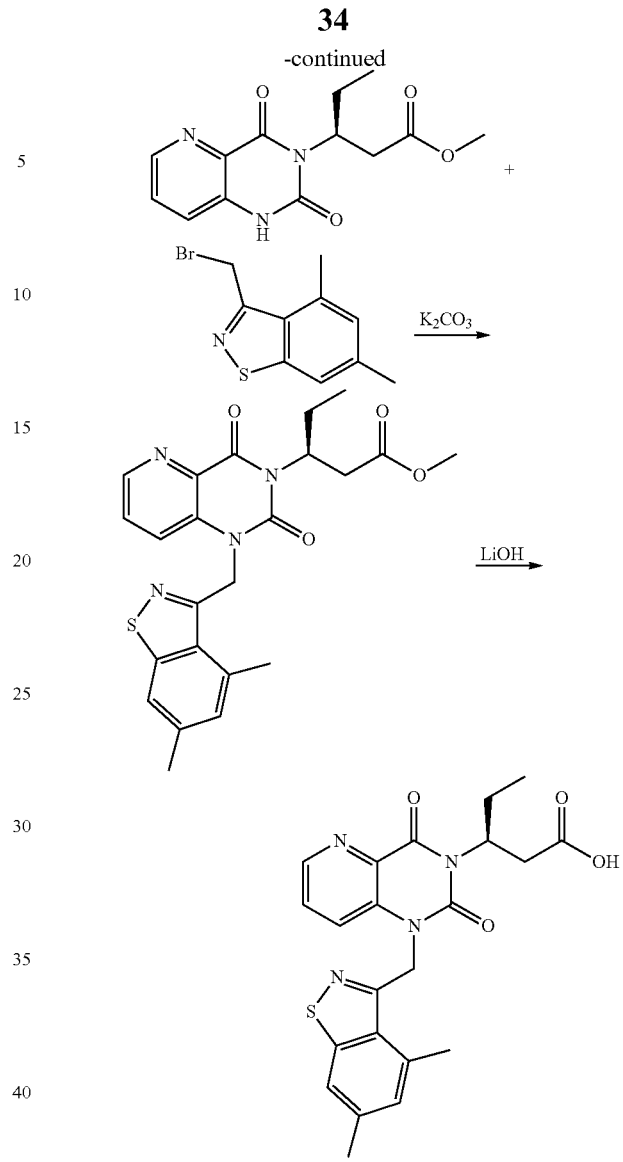

To a solution of 0.6 mL of acetyl chloride in 10 mL of methanol is added 500 mg of (S)-3-aminopentanoic acid at room temperature. The resulting mixture is stirred at 60° C. for 18 h. The mixture is cooled to room temperature and concentrated in vacuo. The resulting light tan oil ((S)-3-aminopentanoic acid methyl ester hydrochloride) is used for the next reaction without further purification. (714 mg, 99%)

To a solution of 321 mg of 3-aminopyridine-2-carboxylic acid in pyridine (5.0 mL) is added 377 mg of 1,1'-carbonyldiimidazole and the mixture is stirred for 2 h at room temperature. The resulting mixture is treated with 300 mg of (S)-3-aminopentanoic acid methyl ester hydrochloride and the mixture is stirred for 16 h at room temperature. Then the solvent is removed under vacuum and the residue is purified by flash chromatography on silica gel to give 250 mg (56%) of (S)-3-[(3-amino-pyridine-2-carbonyl)-amino]-pentanoic acid methyl ester.

To a solution of 250 mg of (S)-3-[(3-amino-pyridine-2-carbonyl)-amino]-pentanoic acid methyl ester in tetrahydrofuran (10 mL) is added 403 mg of 1,1'-carbonyldiimidazole and 0.04 mL of 1,8-diazabicyclo[5.4.0]undec-7-ene at room temperature and the mixture is stirred at room temperature for 60 h. The reaction mixture is diluted with 50 mL of water and the product is extracted with ethyl acetate (50 mL×3). The combined organic layers are dried over sodium sulfate and concentrated. The residue is purified by flash chromatography on silica gel to give 250 mg (91%) of (S)-3-(2,4-dioxo-1,4-dihydro-2H-pyrido[3,2-d]pyrimidin-3-yl)-pentanoic acid methyl ester.

To a solution of 60 mg of (S)-3-(2,4-dioxo-1,4-dihydro-2H-pyrido[3,2-d]pyrimidin-3-yl)-pentanoic acid methyl ester in N,N-dimethylformamide (2.0 mL) is added 66 mg of 3-bromomethyl-4,6-dimethyl-1,2-benzoisothiazole and 36 mg potassium carbonate at room temperature. The mixture is heated to 60° C. for 2.5 h. Then 50 mL of water is added and the product is extracted with ethyl acetate (3×50 mL). The combined organic layers are dried over sodium sulfate and concentrated. The residue is purified by flash chromatography on silica gel to give 80 mg (82%) of (S)-3-[1-(4,6-dimethyl-benzo[d]isothiazol-3-ylmethyl)-2,4-dioxo-1,4-dihydro-2H-pyrido[3,2-d]pyrimidin-3-yl]-pentanoic acid methyl ester.

To a solution of 80 mg of (S)-3-[1-(4,6-dimethyl-benzo[d]isothiazol-3-ylmethyl)-2,4-dioxo-1,4-dihydro-2H-pyrido[3,2-d]pyrimidin-3-yl]-pentanoic acid methyl ester in 1,4-dioxane (2.5 mL) is added lithium hydroxide solution (11 mg of lithium hydroxide monohydrate in 0.5 mL of water) at room temperature. The solution is stirred at the same temperature for 3.5 h. Then 0.5 mL of acetic acid is added along with 25 mL of water. The mixture is extracted with ethyl acetate (3×50 mL). The combined organic layers are dried over sodium sulfate and concentrated. The residue is purified by flash chromatography on silica gel to give 26 mg (34%) of (S)-3-[1-(4,6-dimethyl-benzo[d]isothiazol-3-ylmethyl)-2,4-dioxo-1,4-dihydro-2H-pyrido[3,2-d]pyrimidin-3-yl]-pentanoic acid; LCMS (ESMS): m/z 439.12 (M+H$^+$).

The following compounds are synthesized using a similar procedure.

(S)-3-[1-(4,6-Dimethyl-benzo[d]isothiazol-3-ylmethyl)-2,4-dioxo-1,4-dihydro-2H-pyrido[4,3-d]pyrimidin-3-yl]-pentanoic acid; LCMS (ESMS): m/z 439 (M+H$^+$)

(S)-2-[1-(4,6-Dimethyl-benzo[d]isothiazol-3-ylmethyl)-2,4-dioxo-1,4-dihydro-2H-pyrido[4,3-d]pyrimidin-3-yl]-butyric acid; LCMS (ESMS): m/z 425 (M+H$^+$)

(R)-2-[1-(4,6-Dimethyl-benzo[d]isothiazol-3-ylmethyl)-2,4-dioxo-1,4-dihydro-2H-pyrido[4,3-d]pyrimidin-3-yl]-hexanoic acid; LCMS (ESMS): m/z 453 (M+H$^+$)

(S)-2-[1-(4,6-Dimethyl-benzo[d]isothiazol-3-ylmethyl)-2,4-dioxo-1,4-dihydro-2H-pyrido[4,3-d]pyrimidin-3-yl]-hexanoic acid; LCMS (ESMS): m/z 453 (M+H$^+$)

(R)-2-[1-(4,6-Dimethyl-benzo[d]isothiazol-3-ylmethyl)-2,4-dioxo-1,4-dihydro-2H-pyrido[4,3-d]pyrimidin-3-yl]-pentanoic acid; LCMS (ESMS): m/z 439 (M+H$^+$)

(S)-2-[1-(4,6-Dimethyl-benzo[d]isothiazol-3-ylmethyl)-2,4-dioxo-1,4-dihydro-2H-pyrido[4,3-d]pyrimidin-3-yl]-pentanoic acid; LCMS (ESMS): m/z 439 (M+H$^+$)

(R)-2-[1-(4,6-Dimethyl-benzo[d]isothiazol-3-ylmethyl)-2,4-dioxo-1,4-dihydro-2H-pyrido[4,3-d]pyrimidin-3-yl] pentanoic acid ethyl ester; LCMS (ESMS): m/z 467 (M+H$^+$) (Steps 1-4)

(R)-3-[1-(4,6-Dimethyl-benzo[d]isothiazol-3-ylmethyl)-2,4-dioxo-1,4-dihydro-2H-pyrido[3,4-d]pyrimidin-3-yl]-pentanoic acid; LCMS (ESMS): m/z 439 (M+H$^+$)

(R)-3-[1-(4,6-Dimethyl-benzo[d]isothiazol-3-ylmethyl)-2,4-dioxo-1,4-dihydro-2H-pyrido[4,3-d]pyrimidin-3-yl]-pentanoic acid; LCMS (ESMS): m/z 439 (M+H$^+$)

(R)-3-[1-(4,6-Dimethyl-benzo[d]isothiazol-3-ylmethyl)-2,4-dioxo-1,4-dihydro-2H-pyrido[3,2-d]pyrimidin-3-yl]-pentanoic acid; LCMS (ESMS): m/z 439 (M+H$^+$)

(S)-3-[1-(4,6-Dimethyl-benzo[d]isothiazol-3-ylmethyl)-2,4-dioxo-1,4-dihydro-2H-pyrido[3,4-d]pyrimidin-3-yl]-pentanoic acid; LCMS (ESMS): m/z 439 (M+H$^+$)

(R)-2-[1-(4,6-Dimethyl-benzo[d]isothiazol-3-ylmethyl)-2,4-dioxo-1,4-dihydro-2H-pyrido[4,3-d]pyrimidin-3-yl]-butyric acid; LCMS (ESMS): m/z 425 (M+H$^+$)

Example 3

Synthesis of (R)-3-[2,4-dioxo-1-(1,4,6-trimethyl-1H-indol-3-ylmethyl)-1,4-dihydro-2H-pyrido[3,2-d]pyrimidin-3-yl]-pentanoic acid

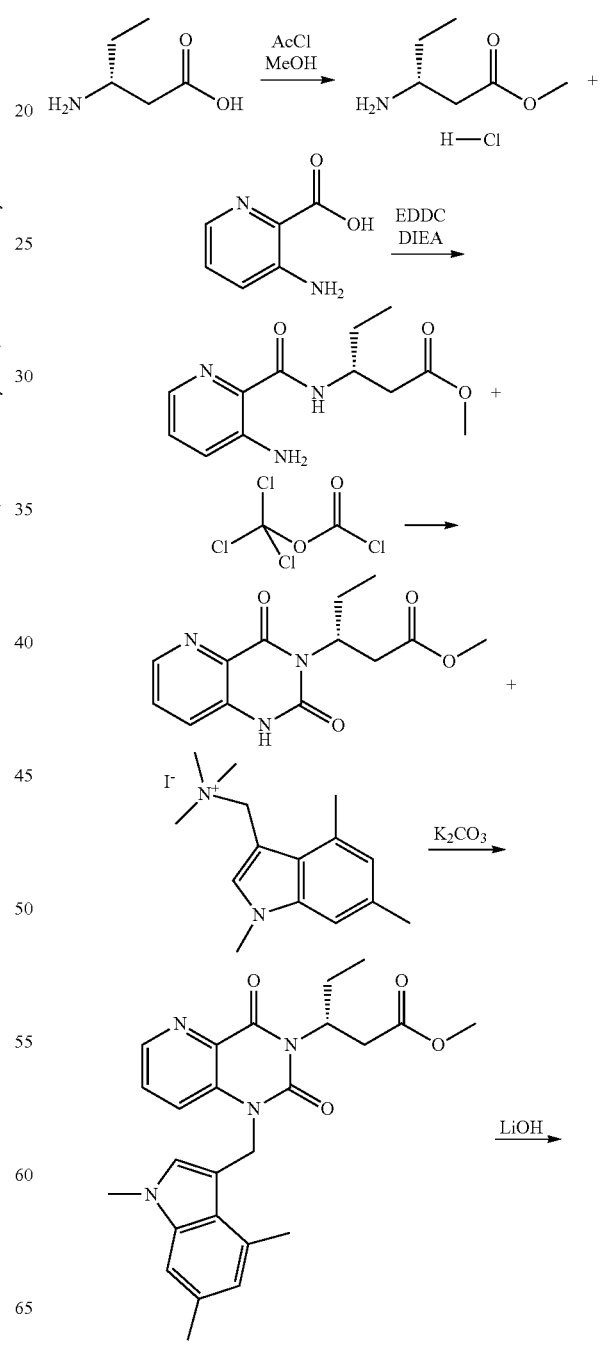

-continued

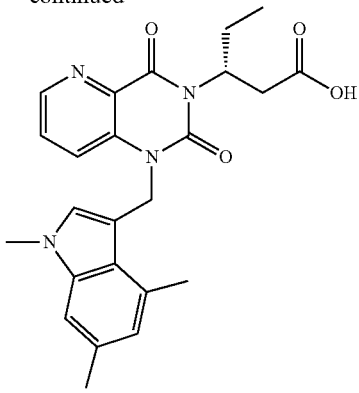

To a solution of 1.45 mL of acetyl chloride in 25 mL of methanol is added 2.0 g of (R)-3-aminopentanoic acid at room temperature. The resulting mixture is stirred at 60° C. for 18 h. The mixture is cooled to room temperature and concentrated in vacuo. The resulting light tan oil ((R)-3-aminopentanoic acid methyl ester hydrochloride) is used for the next reaction without further purification. (2.8 g, 99%)

A mixture of 1 g of 3-aminopyridine-2-carboxylic acid, 950 mg of (R)-3-aminopentanoic acid methyl ester hydrochloride, 1.8 g of N-(3-dimethylaminopropyl)-N'-ethylcarbodiimide, 1.27 g of 1-hydroxybenzotriazole hydrate and 2.3 mL of N,N-diisopropylethylamine in 30 mL of N,N-dimethylformamide is stirred at room temperature for 16 h. The resulting mixture is poured into water and the product was extracted with ethyl acetate. The organic layer is washed with water and brine, dried (sodium sulfate), filtered and concentrated. The residual orange oil ((R)-3-[(3-amino-pyridine-2-carbonyl)-amino]-pentanoic acid methyl ester) is used for the next reaction without further purification. (1.6 g, 88%)

A solution of 1.6 g of (R)-3-[(3-amino-pyridine-2-carbonyl)-amino]-pentanoic acid methyl ester and 0.86 mL of trichloromethyl chloroformate in 25 mL of tetrahydrofuran is stirred at 90° C. for 3 h. The resulting mixture is diluted with saturated sodium bicarbonate solution and the product is extracted with ethyl acetate. The organic layer is washed with water and brine, dried (sodium sulfate), filtered and concentrated. The residue is purified by flash chromatography on silica to give 1.75 g (99%) of (R)-3-(2,4-dioxo-1,4-dihydro-2H-pyrido[3,2-d]pyrimidin-3-yl)-pentanoic acid methyl ester.

A mixture of 1.75 g of (R)-3-(2,4-dioxo-1,4-dihydro-2H-pyrido[3,2-d]pyrimidin-3-yl)-pentanoic acid methyl ester, 2.5 g of trimethyl-(1,4,6-trimethyl-1H-indol-3-ylmethyl)-ammonium iodide and 1.7 g of potassium carbonate in 50 mL of N,N-dimethylformamide is heated at 65° C. for 3 h. The resulting mixture is diluted with water and the product is extracted with ethyl acetate. The organic layer is washed with brine, dried (sodium sulfate) filtered and concentrated. The residue is purified by flash chromatography on silica gel to give 1.0 g (35%) of (R)-3-[2,4-dioxo-1-(1,4,6-trimethyl-1H-indol-3-ylmethyl)-1,4-dihydro-2H-pyrido[3,2-d]pyrimidin-3-yl]-pentanoic acid methyl ester.

A solution of 1.0 g of (R)-3-[2,4-dioxo-1-(1,4,6-trimethyl-1H-indol-3-ylmethyl)-1,4-dihydro-2H-pyrido[3,2-d]pyrimidin-3-yl]-pentanoic acid methyl ester and 187 mg of lithium hydroxide monohydrate in 20 mL water and 20 mL of 1,4-dioxane is stirred at room temperature for 3 h. The resulting mixture is neutralized with 0.26 mL of acetic acid and the resulting mixture is diluted with water. The product is extracted with ethyl acetate. The organic layer is washed with water and brine, dried (sodium sulfate), filtered and concentrated. The residue is purified by flash chromatography on silica gel. The combined fractions are concentrated and the residue is triturated with ether to give 410 mg (42%) of (R)-3-[2,4-dioxo-1-(1,4,6-trimethyl-1H-indol-3-ylmethyl)-1,4-dihydro-2H-pyrido[3,2-d]pyrimidin-3-yl]-pentanoic acid; LCMS (ESMS): m/z 435 (M+H$^+$).

The following compounds are synthesized using a similar procedure.

3-Cyclopropyl-3-[2,4-dioxo-1-(1,4,6-trimethyl-1H-indol-3-ylmethyl)-1,4-dihydro-2H-pyrido[3,2-d]pyrimidin-3-yl]-propionic acid; LCMS (ESMS): m/z 447 (M+H$^+$)

(R)-3-[2,4-Dioxo-1-(1,4,6-trimethyl-1H-indol-3-ylmethyl)-1,4-dihydro-2H-pyrido[4,3-d]pyrimidin-3-yl]-pentanoic acid; LCMS (ESMS): m/z 435 (M+H$^+$)

3-[2,4-Dioxo-1-(1,4,6-trimethyl-1H-indol-3-ylmethyl)-1,4-dihydro-2H-pyrido[3,2-d]pyrimidin-3-yl]-heptanoic acid; LCMS (ESMS): m/z 463 (M+H$^+$)

Example 4

Synthesis of (S)-2-[1-(4,6-Dimethyl-benzo[d]isothiazol-3-ylmethyl)-2,4-dioxo-1,4-dihydro-2H-pyrido[3,2-d]pyrimidin-3-yl]-butyric acid

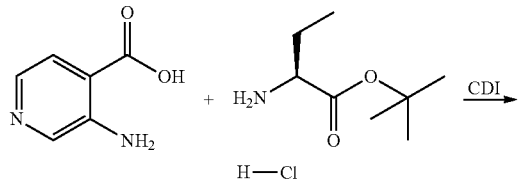

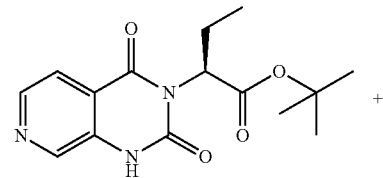

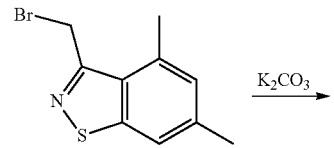

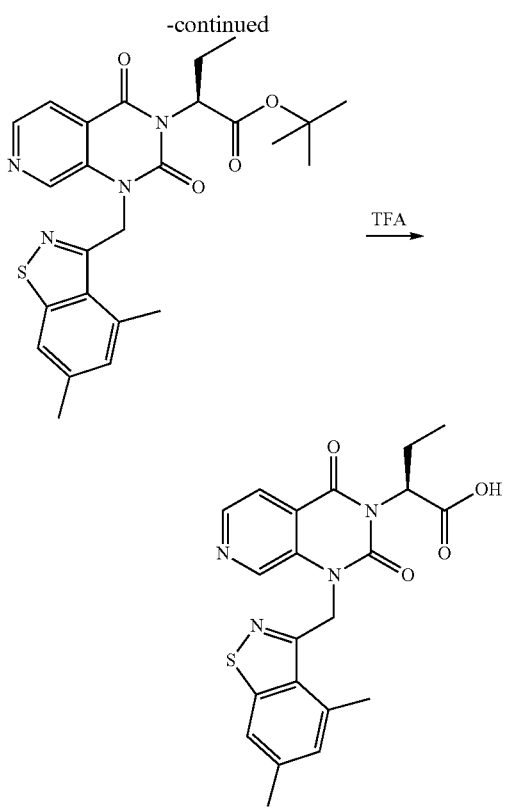

To a solution of 276 mg of 3-aminopyridine-2-carboxylic acid in pyridine (3.0 mL) is added 324 mg of 1,1'-carbonyldiimidazole. The mixture is stirred at room temperature for 2 h. Then 391 mg of (S)-2-amino-butyric acid tert-butyl ester hydrochloride is added and the mixture is stirred for 16 h at room temperature. Then the reaction mixture is diluted with water (1 mL) and concentrated. The residue is diluted with additional 5 mL water and the product is extracted with ethyl acetate (3×5 mL). The combined organic layers are washed with brine, dried (sodium sulfate) and concentrated. The residue is purified by flash chromatography on silica gel to give 218 mg (39%) of (S)-2-[(3-amino-pyridine-2-carbonyl)-amino]-butyric acid tert-butyl ester.

A solution of 217 mg of (S)-2-[(3-amino-pyridine-2-carbonyl)-amino]-butyric acid tert-butyl ester in tetrahydrofuran (10 mL) is treated with 259 mg of 1,1'-carbonyldiimidazole and 0.018 mL of 1,8-diazabicyclo[5.4.0]undec-7-ene. The mixture is stirred at room temperature for 16 h. Then the reaction mixture is added water (1 mL) and the resulting mixture is concentrated and purified by flash chromatography on silica gel to give 130 mg (55%) of (S)-2-(2,4-dioxo-1,4-dihydro-2H-pyrido[3,2-d]pyrimidin-3-yl)-butyric acid tert-butyl ester.

A mixture of 46 mg of (S)-2-(2,4-dioxo-1,4-dihydro-2H-pyrido[3,2-d]pyrimidin-3-yl)-butyric acid tert-butyl ester, 41 mg of 3-bromomethyl-4,6-dimethyl-1,2-benzoisothiazole and 111 mg of potassium carbonate is stirred at room temperature for 4 h. The reaction mixture is diluted with water and the product is filtered and washed with water. The isolated solid is purified by flash chromatography on silica gel to give 72 mg (99%) of (S)-2-[1-(4,6-dimethyl-benzo[d]isothiazol-3-ylmethyl)-2,4-dioxo-1,4-dihydro-2H-pyrido[3,2-d]pyrimidin-3-yl]-butyric acid tert-butyl ester.

A solution of 32 mg of (S)-2-[1-(4,6-dimethyl-benzo[d]isothiazol-3-ylmethyl)-2,4-dioxo-1,4-dihydro-2H-pyrido[3,2-d]pyrimidin-3-yl]-butyric acid tert-butyl ester in 20% trifluoroacetic acid in dichloromethane (1 mL) is stirred at room temperature for 45 min. The resulting mixture is concentrated to give 25 mg (89%) of (S)-2-[1-(4,6-Dimethyl-benzo[d]isothiazol-3-ylmethyl)-2,4-dioxo-1,4-dihydro-2H-pyrido[3,2-d]pyrimidin-3-yl]-butyric acid; LCMS (ESMS): m/z 426 (M+H$^+$).

Methods of Use

In accordance with the invention, there are provided methods of using the compounds as described herein and their pharmaceutically acceptable derivatives. The compounds used in the invention inhibit Chymase. Since Chymase is known to transform angiotensin I to angiotensin II and may contribute to activation of TGF-β, matrix proteases and cytokines, the inhibition of Chymase is an attractive means for preventing and treating a variety of diseases or conditions. Examples include heart failure including chronic heart failure (non-ischemic), post-myocardial infarction heart failure (ischemic), acute myocardial infarction, reperfusion injury, left ventricular dysfunction, cardiac fibrosis, diastolic heart failure and hypertrophic cardiomyopathy, hypertension including pulmonary hypertension, systolic hypertension and resistant hypertension, including coronary artery disease, peripheral arterial occlusive disease, aneurism, stable/unstable angina, restenosis, diabetic nephropathy, atrial fibrillation/ventricular arrhythmias, valvular heart disease, pericardial diseases, renal insufficiency (chronic kidney disease, end stage renal disease), stroke. The compounds of the invention may also be useful for the following procedures: coronary artery bypass grafting, percutaneous coronary intervention and stenting.

Other diseases within the scope of the invention include allergic rhinitis, dermatitis, asthma, chronic obstructive pulmonary disease (COPD), and pulmonary inflammation, asthma, osteoarthritis, bone resorption diseases, multiple sclerosis, Guillain-Barre syndrome, Crohn's disease, ulcerative colitis, psoriasis, graft versus host disease, systemic lupus erythematosus, rheumatoid arthritis, toxic shock syndrome, Alzheimer's disease, inflammatory bowel diseases, acute and chronic pain as well as symptoms of inflammation, thermal injury, adult respiratory distress syndrome (ARDS), multiple organ injury secondary to trauma, acute glomerulonephritis, dermatoses with acute inflammatory components, acute purulent meningitis or other central nervous system disorders, syndromes associated with hemodialysis, leukopherisis, granulocyte transfusion associated syndromes, and necrotizing entrerocolitis, traumatic arthritis, and sepsis. Reference in this regard may be made to U.S. Pat. No. 5,948,785; U.S. Pat. No. 6,271,238; U.S. Pat. No. 5,691,335; U.S. Pat. No. 5,814,631; U.S. Pat. No. 6,300,337; EP 1,099,690; U.S. Pat. No. 6,323,219; US 2005-0245536 A1; Fukami, et al., *Current Pharmaceutical Design* 1998, vol. 4, pp. 439-453.

As disclosed in the Background of the Invention, the compounds of the invention may contribute to activation of cytokines, they will therefore be useful for treating oncological diseases. Reference in this regard may be made to US 2005-0245536 A1. These diseases include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma and mesothelioma.

Examples of brain cancers include, but are not limited to brain stem, optic and hypophtalmic glioma, cerebella and cerebral astrocytoma, medulloblastoma, ependymoma, as well as pituitary, neuroectodermal and pineal tumor.

Examples of peripheral nervous system tumors include, but are not limited to neuroblastoma, ganglioneuroblastoma, and peripheral nerve sheath tumors.

Examples of tumors of the endocrine and exocrine system include, but are not limited to thyroid carcinoma, adrenocortical carcinoma, pheochromocytoma, and carcinoid tumors.

Tumors of the male reproductive organs include, but are not limited to prostate and testicular cancer.

Tumors of the female reproductive organs include, but are not limited to endometrial, cervical, ovarian, vaginal.

These disorders have been well characterized in man, but also exist with a similar etiology in other mammals, and can be treated by pharmaceutical compositions of the present invention.

For therapeutic use, the compounds may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds described herein may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Combinations with other therapeutics include but are not limited to: angiotensin II receptor blockers, angiotensin converting enzyme inhibitors, CETP inhibitors/apoA1 mimetics, adenosine diphosphate (P2Y12) inhibitors, direct thrombin inhibitors, aldosterone antagonists, factor Xa inhibitors, natriuretic peptides (ANP/BNP), renin inhibitors, anti-arrhythmics, Chymase inhibitors, HMG-CoA Reductase inhibitors (Statins), Rho kinase inhibitors, beta-blockers, Lipoprotein-associated phospholipase A2 inhibitors, cardiac glycosides, calcium channel blockers, diuretics, fibrates, Endothelin Receptor Antagonists, GPIIb/IIIa inhibitors, histone deacetylase inhibitors, heparins, nicotinic acid derivatives, vasopeptidase inhibitors, nitrites and nitrates, fatty acid oxidation inhibitors, oral anticoagulants, acyl-CoA:cholesterol acyltransferase inhibitors, thrombolytics, microsomal triglyceride transfer protein inhibitors, thiazolidinediones, adenosine receptor modulators, cholesterol absorbtion inhibitors, Advanced Glycation End products/receptor (AGE/RAGE) interaction modulators/blockers, acetyl salicylic acid, dipyridamole, gene therapy and cell therapy.

Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound (w/w) or a combination thereof. The optimum percentage (w/w) of a compound of the invention may vary and is within the purview of those skilled in the art. Alternatively, the compounds may be administered separately (either serially or in parallel). Separate dosing allows for greater flexibility in the dosing regime.

As mentioned above, dosage forms of the above-described compounds include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). Dosage levels and requirements are well-recognized in the art and may be selected by those of ordinary skill in the art from available methods and techniques suitable for a particular patient. In some embodiments, dosage levels range from about 1-1000 mg/dose for a 70 kg patient.

Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

The term "patient" includes both human and non-human mammals.

The term "effective amount" means an amount of a compound according to the invention which, in the context of which it is administered or used, is sufficient to achieve the desired effect or result. Depending on the context, the term effective amount may include or be synonymous with a pharmaceutically effective amount or a diagnostically effective amount.

The terms "pharmaceutically effective amount" or "therapeutically effective amount" means an amount of a compound according to the invention which, when administered to a patient in need thereof, is sufficient to effect treatment for disease-states, conditions, or disorders for which the compounds have utility. Such an amount would be sufficient to elicit the biological or medical response of a tissue, system, or patient that is sought by a researcher or clinician. The amount of a compound of according to the invention which constitutes a therapeutically effective amount will vary depending on such factors as the compound and its biological activity, the composition used for administration, the time of administration, the route of administration, the rate of excretion of the compound, the duration of treatment, the type of disease-state or disorder being treated and its severity, drugs used in combination with or coincidentally with the compounds of the invention, and the age, body weight, general health, sex, and diet of the patient. Such a therapeutically effective amount can be determined routinely by one of ordinary skill in the art having regard to their own knowledge, the prior art, and this disclosure.

The term "diagnostically effective amount" means an amount of a compound according to the invention which, when used in a diagnostic method, apparatus, or assay, is sufficient to achieve the desired diagnostic effect or the desired biological activity necessary for the diagnostic method, apparatus, or assay. Such an amount would be sufficient to elicit the biological or medical response in a diagnostic method, apparatus, or assay, which may include a biological or medical response in a patient or in a in vitro or in vivo tissue or system, that is sought by a researcher or clinician. The amount of a compound according to the invention which constitutes a diagnostically effective amount will vary depending on such factors as the compound and its biological activity, the diagnostic method, apparatus, or assay used, the composition used for administration, the time of administration, the route of administration, the rate of excretion of the compound, the duration of administration, drugs and other compounds used in combination with or coincidentally with the compounds of the invention, and, if a patient is the subject of the diagnostic administration, the age, body weight, general health, sex, and diet of the patient. Such a diagnostically effective amount can be determined routinely by one of ordinary skill in the art having regard to their own knowledge, the prior art, and this disclosure.

The terms "treating" or "treatment" mean the treatment of a disease-state in a patient, and include:
(i) preventing the disease-state from occurring in a patient, in particular, when such patient is genetically or otherwise predisposed to the disease-state but has not yet been diagnosed as having it;
(ii) inhibiting or ameliorating the disease-state in a patient, i.e., arresting or slowing its development; or
(iii) relieving the disease-state in a patient, i.e., causing regression or cure of the disease-state.

In Vitro Assay for Inhibition of Chymase

Chymase assays were performed in a total volume of 15 μL in Corning black opaque 384-well microtiter plates with a non-binding surface (Corning, N.Y.). The assay buffer was comprised of 20 mM Tris HCl pH 8.0, 50 mM NaCl, 0.01% CHAPS. The test compounds were serially diluted 3-fold with neat DMSO in a 96-well polypropylene plate from a 10 mM DMSO stock to give the 10 point dose response curve. 3 μL of the resulting DMSO solution were transferred to a 384-well polypropylene plate in duplicate, and 37 μL of assay buffer was added. Chymase was added to the assay plate in 3 uL of assay buffer followed by 2 uL of the appropriate compound dilution using a PlateMate Plus (Matrix Technologies Corp., Hudson, N.H.). The reaction was initiated by the addition of 10 uL rhodamine 110, bis-(succinoyl-L-alanyl-L-alanyl-L-prolyl-L-phenylalanylamide) (American Peptides, Sunnyvale, Calif.) in assay buffer containing 150 μM tris(2-carboxyethyl)phosphine (TCEP, Pierce Chemical, Rockford, Ill.) using a Multidrop (Thermo Electron Corp., Waltham, Mass.). Final assay concentrations were 500 μM chymase, 100 nM substrate, 100 μM TCEP, and 1% DMSO. The plates were incubated at 28° C. and 80% humidity for 1 hour, at which time the fluorescence was read on a Viewlux 1430 Microplate Imager (Perkin Elmer Life Sciences, Boston, Mass.) with 485 nm excitation, 530 nm emission, and a fluorescein dichroic mirror. The percentage of control values were calculated relative to assay blanks containing complete reaction minus chymase and a 100% control containing assay buffer with 1% DMSO in place of compound. IC50 values were obtained by fitting the data using XLFit4 (IDBS Software).

Preferred compounds of the invention have an IC50 activity of 50 nanoMolar (nM) or less.

All patent and literature references cited in this application are incorporated herein by reference in their entirety.

The invention claimed is:

1. A compound of the formula (I):

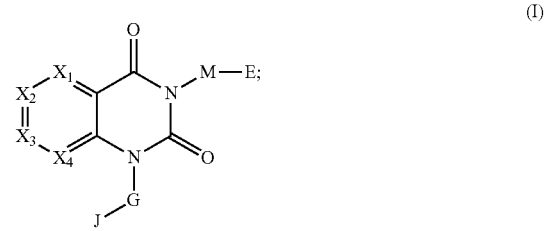

wherein $X_1$, $X_2$, $X_3$ and $X_4$ are each independently —CH— or nitrogen, with the proviso that at least one of them is nitrogen;

E is —COOH or —COOR wherein R is $C_1$-$C_5$ alkyl;

G is $C_1$-$C_2$ alkyl;

J is a heteroaryl group optionally substituted with 1-3 substituents chosen from halogen, $C_1$-$C_3$ alkyl and $C_1$-$C_3$ alkoxy;

M is $C_1$-$C_5$ alkyl optionally substituted with 1-3 substitutents chosen from $C_1$-$C_5$ alkyl and $C_3$-$C_6$ carbocycle;

or a pharmaceutically acceptable salt thereof.

2. The compound according to claim 1 and wherein:

E is —COOH or —COOR wherein R is $C_1$-$C_3$ alkyl;

G is —$CH_2$—;

J is a heteroaryl group chosen from indolyl, benzothiazolyl and benzoisothiazolyl each optionally substituted with 1-3 $C_1$-$C_3$ alkyl groups;

M is $C_1$-$C_3$ alkyl optionally substituted with 1-3 substitutents chosen from $C_1$-$C_5$ alkyl, phenyl and cyclopropyl.

3. The compound according to claim 2 and wherein:

E is —COOH;

J is a heteroaryl group chosen from indolyl and benzoisothiazolyl each optionally substituted with 1-3 methyl groups;

M is $C_1$-$C_2$ alkyl optionally substituted with 1-3 substitutents chosen from $C_1$-$C_5$ alkyl, phenyl and cyclopropyl.

4. The compound according to claim 3 and wherein:

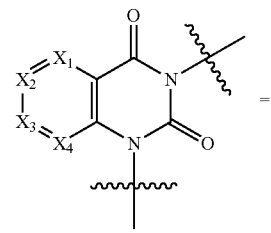

-continued
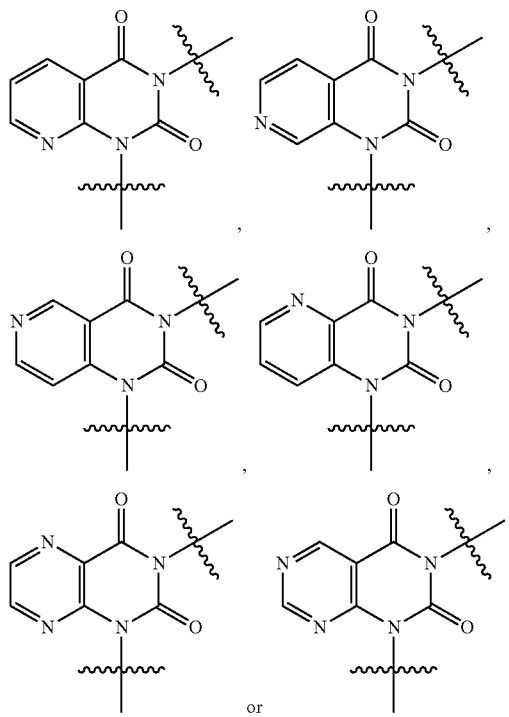
J is a heteroaryl group chosen from indolyl or benzoisothiazolyl each optionally substituted with 2-3 methyl groups;
M is $C_1$-$C_2$ alkyl optionally substituted with 1 substitutent chosen from $C_1$-$C_5$ alkyl, phenyl and cyclopropyl.
5. The compound according to claim 4 and wherein:
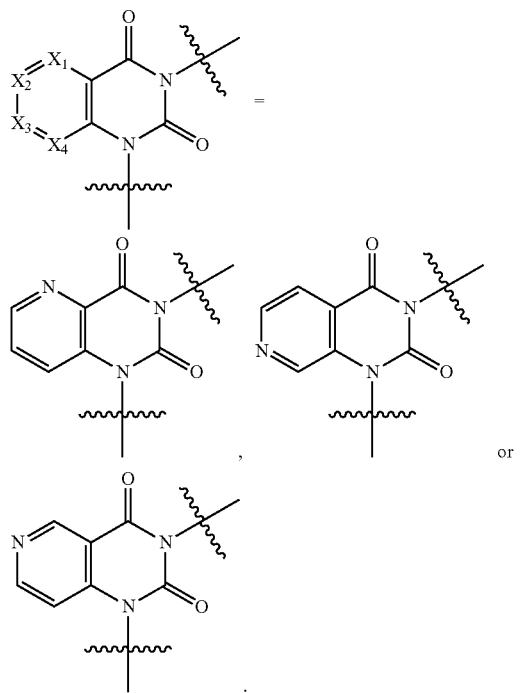
6. The compound according to claim 5 and wherein:
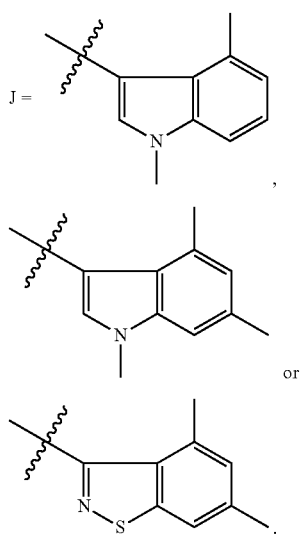
7. A compound chosen from
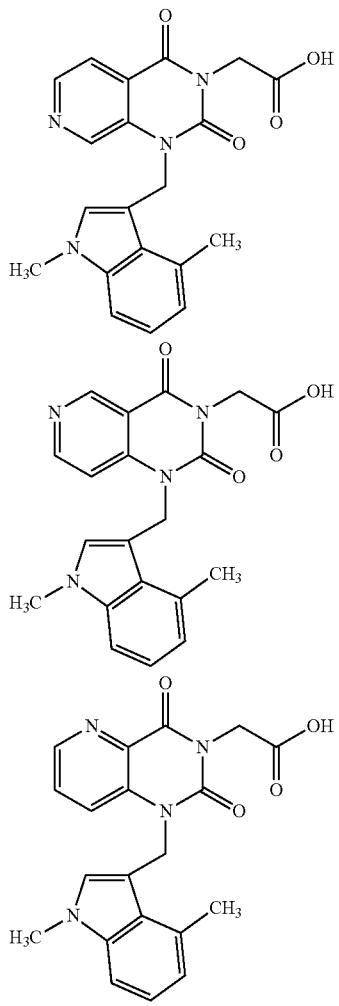

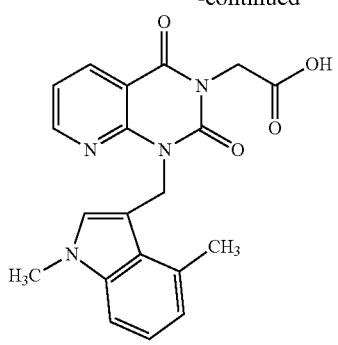
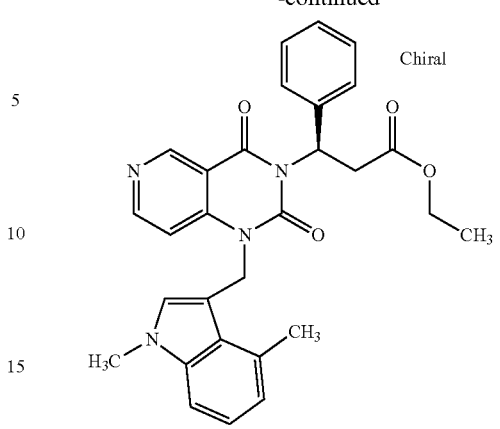
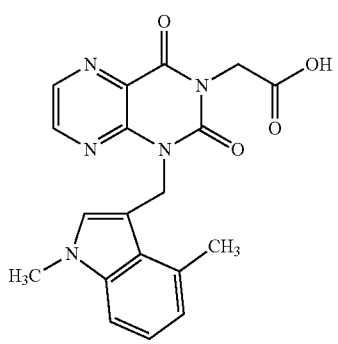
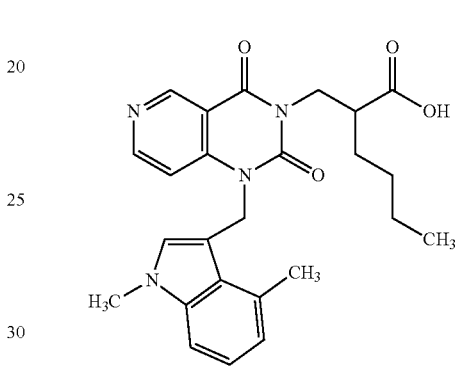
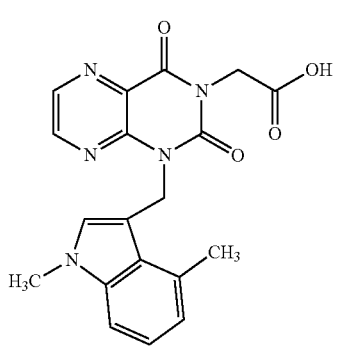
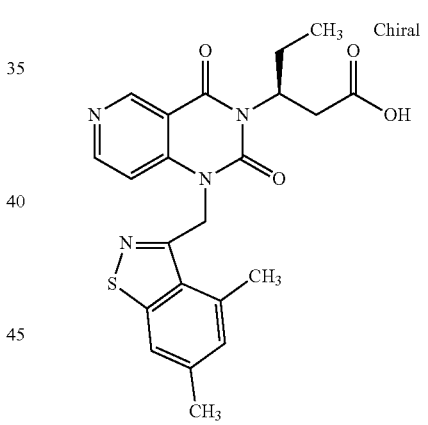
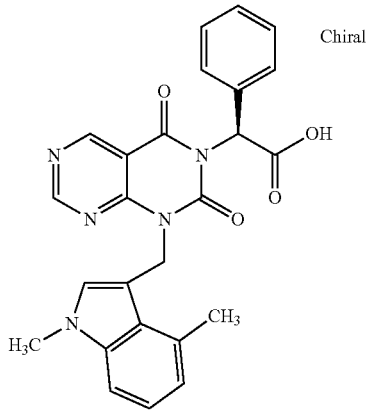
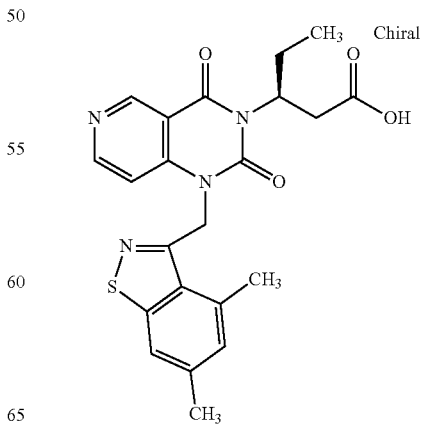

49
-continued
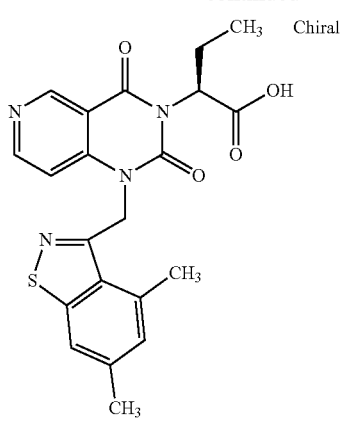
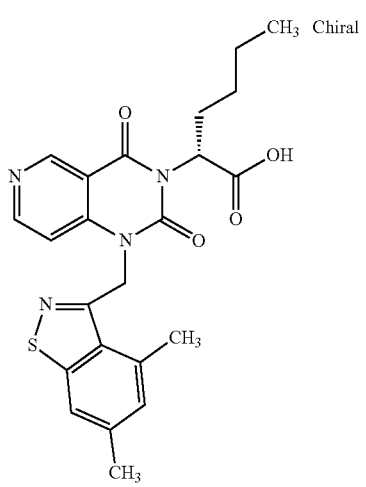
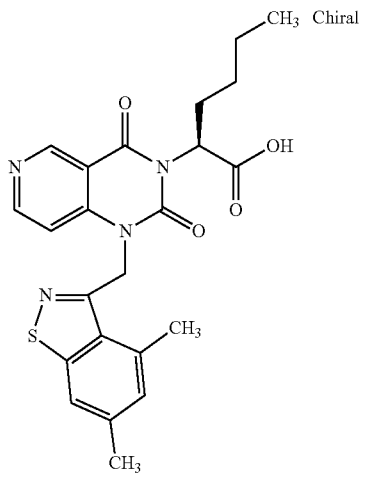
50
-continued
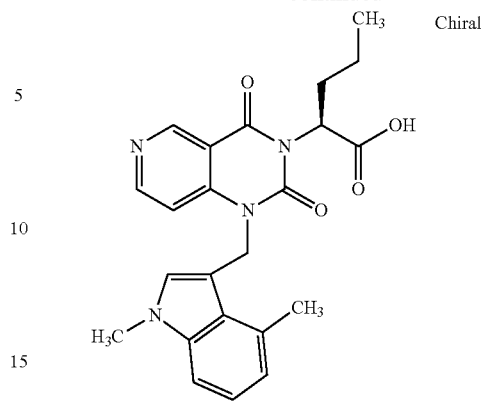
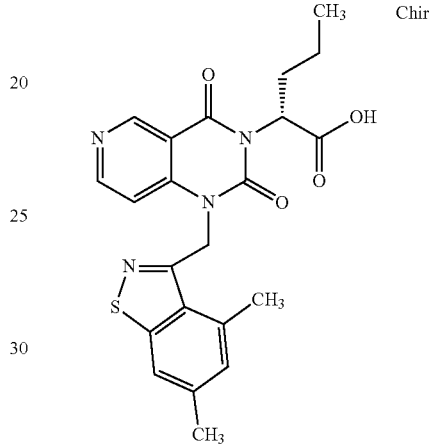
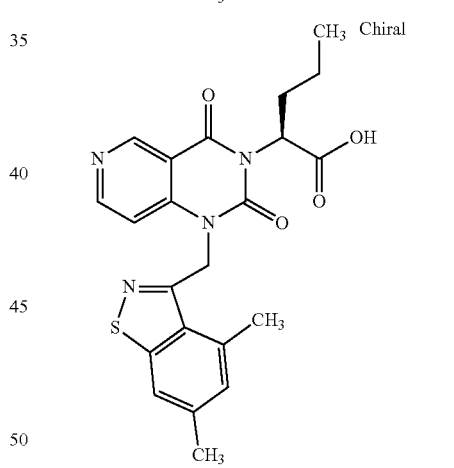
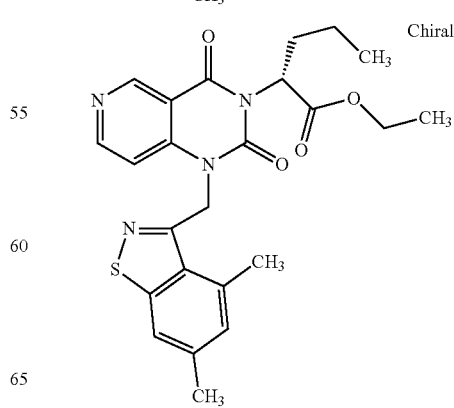

51
-continued
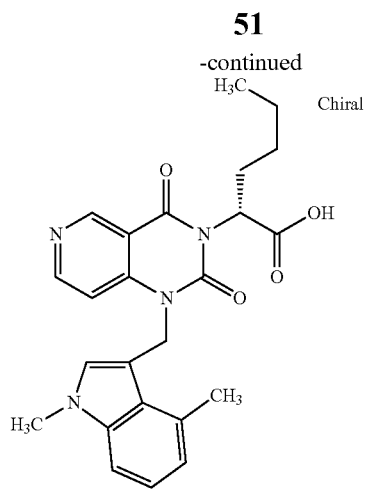
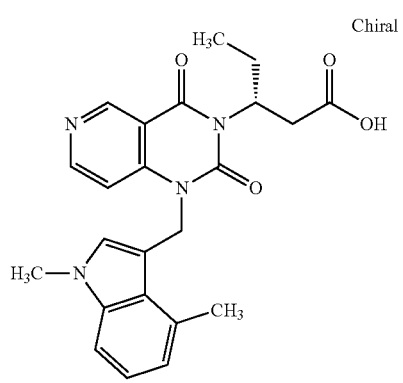
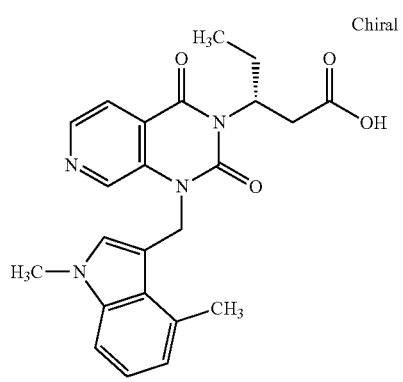
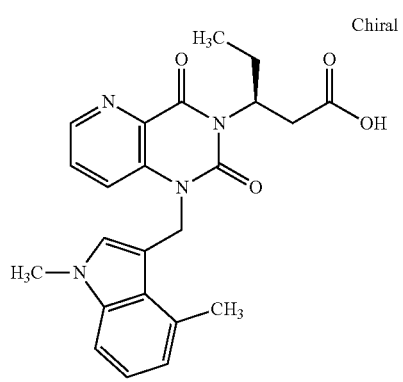
52
-continued
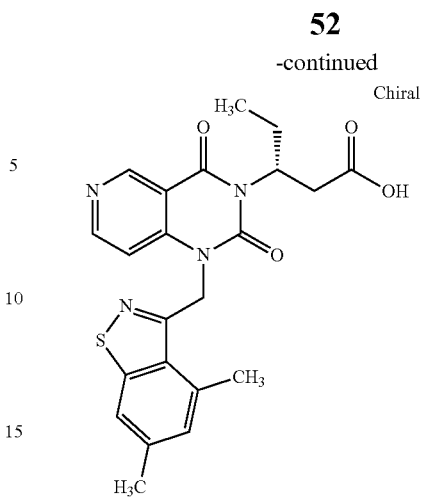
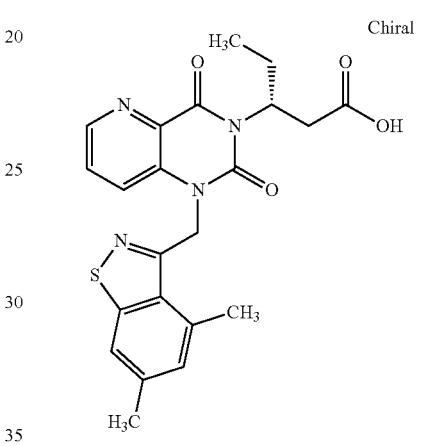
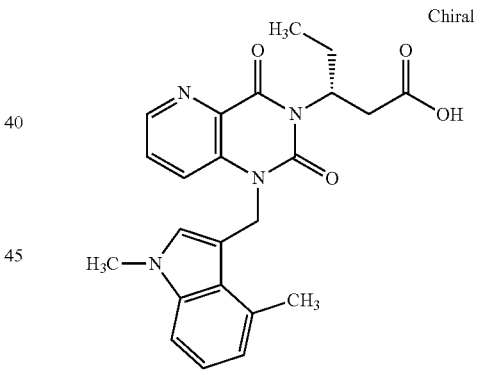
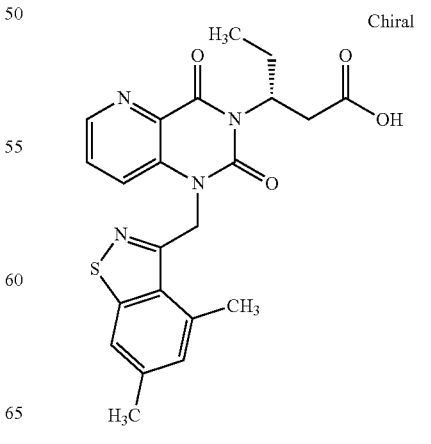

53
-continued
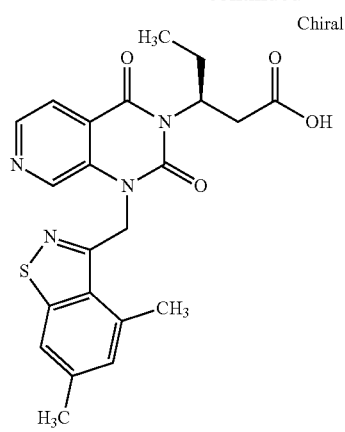
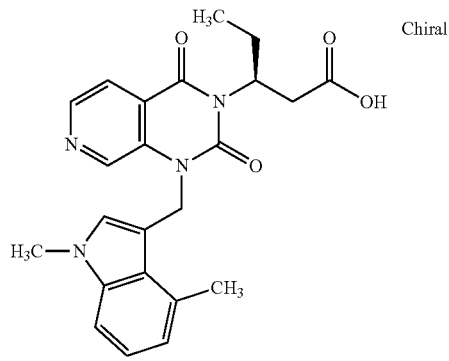
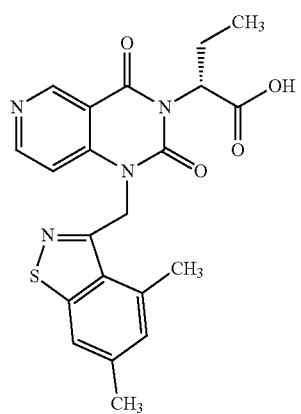
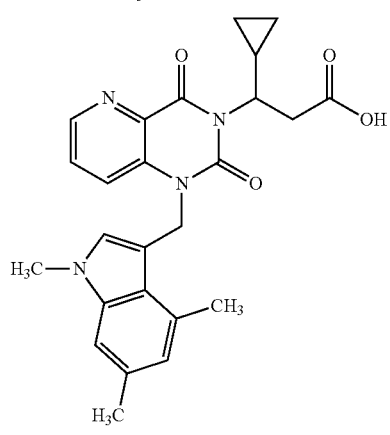
54
-continued
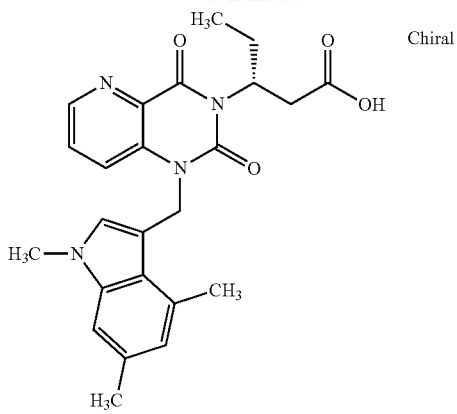
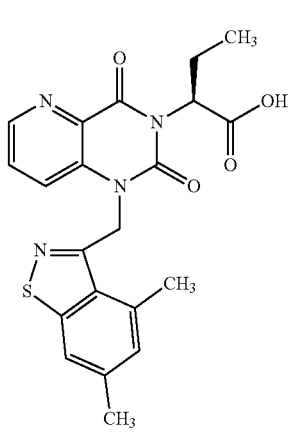
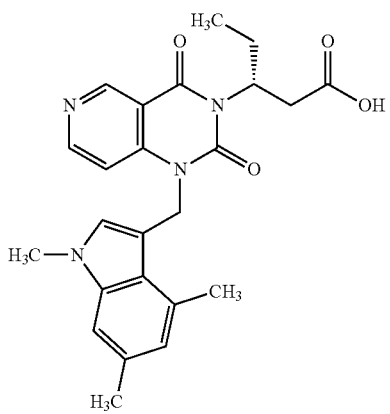
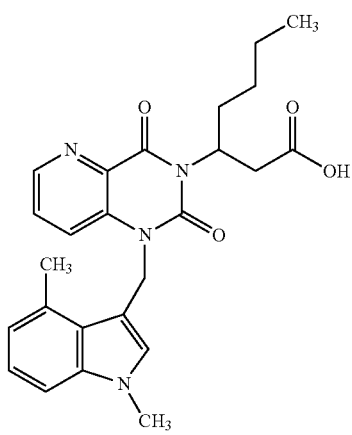

-continued
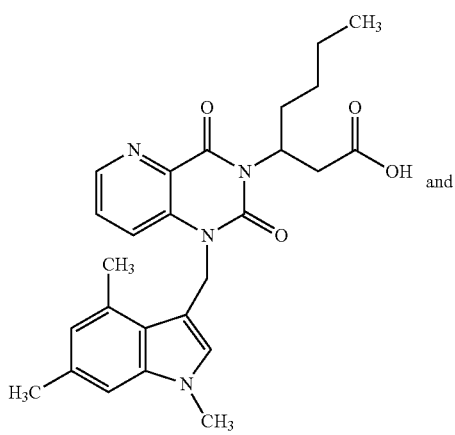 and
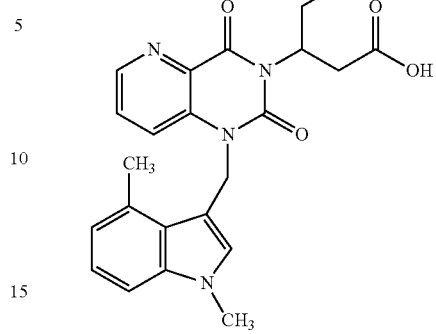
or a pharmaceutically acceptable salt thereof.
8. A pharmaceutical composition comprising a therapeutically effective amount of a compound according to claim 1 and one or more pharmaceutically acceptable carries and/or adjuvants.
* * * * *